United States Patent
Bartlett et al.

(10) Patent No.: US 11,423,164 B2
(45) Date of Patent: Aug. 23, 2022

(54) MULTIPLE ELECTRONIC SIGNATURE METHOD

(71) Applicant: Vynca, Inc., Palo Alto, CA (US)

(72) Inventors: Rush Bartlett, Mountain View, CA (US); Ashish Kaul, Fremont, CA (US); Ryan Van Wert, San Francisco, CA (US); Frank Wang, Taipei (TW); Tsung-Wei Wang, Taipei (TW)

(73) Assignee: Vynca, Inc., Palo Alto, CA (US)

( * ) Notice: Subject to any disclaimer, the term of this patent is extended or adjusted under 35 U.S.C. 154(b) by 432 days.

(21) Appl. No.: 16/418,050

(22) Filed: May 21, 2019

(65) Prior Publication Data

US 2019/0354706 A1    Nov. 21, 2019

Related U.S. Application Data

(60) Provisional application No. 62/674,136, filed on May 21, 2018.

(51) Int. Cl.

| | |
|---|---|
| *G06F 21/62* | (2013.01) |
| *G16H 10/60* | (2018.01) |
| *G06F 3/0484* | (2022.01) |
| *G06F 40/171* | (2020.01) |
| *G06F 21/64* | (2013.01) |

(Continued)

(52) U.S. Cl.
CPC ........ *G06F 21/6209* (2013.01); *G06F 3/0484* (2013.01); *G06F 21/64* (2013.01); *G06F 40/171* (2020.01); *G06F 40/174* (2020.01); *G06Q 50/18* (2013.01); *G06V 40/30* (2022.01); *G16H 10/60* (2018.01); *H04L 9/32* (2013.01)

(58) Field of Classification Search
None
See application file for complete search history.

(56) References Cited

U.S. PATENT DOCUMENTS

| | | |
|---|---|---|
| 6,460,770 B1 | 10/2002 | Kucharczyk |
| 7,542,912 B1 | 6/2009 | Durand |

(Continued)

FOREIGN PATENT DOCUMENTS

| | | |
|---|---|---|
| WO | WO 2008084248 | 7/2008 |
| WO | WO 2013093864 | 6/2013 |
| WO | WO 2014124014 | 8/2014 |

OTHER PUBLICATIONS

Sherman, "Computer-assisted creation of psychiatric advance directives," Community Ment Health J., 34(4):351-362, Aug. 1998.

(Continued)

*Primary Examiner* — Howard Cortes
(74) *Attorney, Agent, or Firm* — Merchant & Gould P.C.

(57) ABSTRACT

Examples disclosed herein include a method for securely collecting and managing document data is disclosed. First handwriting data is received from a first user device. Responsive to receiving the first handwriting data, an additional handwriting data security process is initiated. After initiating the additional handwriting data security process, additional handwriting data is received from a second user device. Based on the additional handwriting data security process, the first handwriting data is accepted or rejected. After accepting the first handwriting data, a document is generated with the first handwriting data and the additional handwriting data being applied to the document.

19 Claims, 30 Drawing Sheets

(51) Int. Cl.
*H04L 9/32* (2006.01)
*G06F 40/174* (2020.01)
*G06Q 50/18* (2012.01)
*G06V 40/30* (2022.01)

(56) References Cited

U.S. PATENT DOCUMENTS

| | | | |
|---|---|---|---|
| 7,620,244 B1* | 11/2009 | Collier | G06K 9/00187 |
| | | | 382/119 |
| 8,306,830 B1 | 11/2012 | Renuart et al. | |
| 8,468,610 B2 | 6/2013 | Beals | |
| 9,286,482 B1 | 3/2016 | Dumont | |
| 9,679,190 B2 | 6/2017 | Bartlett | |
| 9,881,201 B2 | 1/2018 | Bartlett | |
| 10,043,056 B1* | 8/2018 | Danyluk | G06K 9/00181 |
| 10,425,230 B1 | 9/2019 | Tang et al. | |
| 2002/0133470 A1 | 9/2002 | Gruber | |
| 2003/0140252 A1* | 7/2003 | Lafon | H04L 9/3247 |
| | | | 726/10 |
| 2003/0229515 A1 | 12/2003 | Rizvi | |
| 2005/0021376 A1 | 1/2005 | Zaleski | |
| 2005/0027544 A1 | 2/2005 | Newstead et al. | |
| 2005/0102520 A1 | 5/2005 | Baxter et al. | |
| 2005/0132196 A1* | 6/2005 | Dietl | H04L 9/3236 |
| | | | 713/176 |
| 2005/0187794 A1 | 8/2005 | Kimak | |
| 2006/0071081 A1 | 4/2006 | Wang | |
| 2006/0072144 A1 | 4/2006 | Dowling et al. | |
| 2006/0161973 A1 | 7/2006 | Royer | |
| 2006/0184865 A1 | 8/2006 | Chakraborty | |
| 2006/0287890 A1 | 12/2006 | Stead | |
| 2007/0033092 A1 | 2/2007 | Iams | |
| 2007/0130084 A1 | 6/2007 | Kay | |
| 2007/0188793 A1* | 8/2007 | Wakai | G06K 9/00161 |
| | | | 358/1.14 |
| 2007/0206248 A1 | 9/2007 | Winterbottom et al. | |
| 2008/0072334 A1 | 3/2008 | Bailey et al. | |
| 2008/0243599 A1 | 10/2008 | Kwak | |
| 2009/0025087 A1* | 1/2009 | Peirson, Jr. | G06Q 10/00 |
| | | | 726/27 |
| 2009/0037224 A1 | 2/2009 | Raduchel | |
| 2009/0132351 A1 | 5/2009 | Gibson | |
| 2009/0164255 A1* | 6/2009 | Menschik | G16H 70/20 |
| | | | 705/3 |
| 2010/0031140 A1* | 2/2010 | Cummins | H04L 9/3247 |
| | | | 715/236 |
| 2010/0100743 A1* | 4/2010 | Ali | H04L 9/3247 |
| | | | 713/176 |
| 2010/0161993 A1* | 6/2010 | Mayer | H04N 1/32112 |
| | | | 713/178 |
| 2010/0217996 A1 | 8/2010 | Ross et al. | |
| 2010/0299437 A1 | 11/2010 | Moore | |
| 2011/0246230 A1* | 10/2011 | Sie | G06F 21/6245 |
| | | | 705/3 |
| 2011/0271332 A1* | 11/2011 | Jones | H04L 9/3247 |
| | | | 726/7 |
| 2012/0061458 A1 | 3/2012 | Bahr | |
| 2012/0284591 A1 | 11/2012 | Seed | |
| 2013/0185098 A1 | 7/2013 | Mitchel et al. | |
| 2013/0185210 A1 | 7/2013 | Dodson | |
| 2013/0334298 A1 | 12/2013 | Sakpal | |
| 2014/0019761 A1* | 1/2014 | Shapiro | H04L 9/3247 |
| | | | 713/176 |
| 2014/0221795 A1 | 8/2014 | Yeager | |
| 2014/0275807 A1 | 9/2014 | Redei | |
| 2014/0317080 A1 | 10/2014 | Piraino et al. | |
| 2015/0010216 A1* | 1/2015 | Papastefanou | G06K 9/00154 |
| | | | 382/120 |
| 2015/0199389 A1 | 7/2015 | Morrison et al. | |
| 2015/0213404 A1 | 7/2015 | Follis | |
| 2015/0242812 A1 | 8/2015 | Nelson | |
| 2015/0264564 A1* | 9/2015 | Vanderhulst | H04W 12/08 |
| | | | 726/3 |
| 2015/0271179 A1 | 9/2015 | Wang | |
| 2015/0294068 A1* | 10/2015 | Bartlett, II | G16H 10/60 |
| | | | 705/51 |
| 2015/0347681 A1 | 12/2015 | Bartlett | |
| 2016/0006715 A1* | 1/2016 | Lee | H04L 63/083 |
| | | | 713/155 |
| 2016/0012556 A1 | 1/2016 | Moore et al. | |
| 2016/0048696 A1* | 2/2016 | Follis | G06F 21/6209 |
| | | | 726/28 |
| 2016/0219027 A1 | 7/2016 | Kaplan | |
| 2016/0224962 A1* | 8/2016 | Herwig | G06Q 20/206 |
| 2016/0226829 A1 | 8/2016 | Steeves et al. | |
| 2016/0232214 A1 | 8/2016 | Bonda et al. | |
| 2016/0328523 A1* | 11/2016 | Bartlett, II | H04L 63/061 |
| 2017/0135142 A1 | 5/2017 | Bartlett | |
| 2017/0213069 A1* | 7/2017 | Giron Espon | B42D 25/318 |
| 2018/0053265 A1 | 2/2018 | Lyon | |
| 2018/0089412 A1* | 3/2018 | Kopikare | G06F 21/32 |
| 2018/0139204 A1 | 5/2018 | Votaw et al. | |
| 2018/0212782 A1* | 7/2018 | Csik | G06F 21/6272 |
| 2018/0247108 A1* | 8/2018 | Hong | G06K 9/00416 |
| 2018/0260678 A1* | 9/2018 | Edwards | G06K 19/18 |
| 2018/0270070 A1 | 9/2018 | Altman et al. | |
| 2018/0285838 A1* | 10/2018 | Franaszek | G06Q 20/42 |
| 2018/0285983 A1* | 10/2018 | Franaszek | G06Q 40/12 |
| 2019/0163957 A1 | 5/2019 | Bartlett | |
| 2019/0311021 A1* | 10/2019 | Hayslett | G06F 40/143 |
| 2020/0047865 A1* | 2/2020 | Alsina | B63H 20/02 |
| 2020/0169415 A1* | 5/2020 | Schmidt | H04L 9/3247 |
| 2020/0258176 A1* | 8/2020 | Gibson | H04L 9/3239 |
| 2020/0403984 A1* | 12/2020 | Minehan | H04L 9/3239 |

OTHER PUBLICATIONS

Softpro GmbH, "E-Signing on iPad," Retrieved from the Internet URL: https://web.archive.org/web/20120915105226/http://www.softpro.de/data/anonymous_successstories/softpro_insurance_success_story_aia_en.pdf, Retrieved on Jun. 11, 2014 XP055122592, Feb. 1, 2012, 2 pages.

Softpro GmbH, "Samsung Galaxy Note & ATIV PCs: Electronic Signature with SignDoc Mobile," Retrieved from the Internet: URL: http://www.slideshare.net/SOFTPROGroup/softpro-signdoc-mobile-app-on-samsung-galaxy-note-electronic-signing, retrieved on Jun. 11, 2014 XP055122653, Apr. 2, 2012, 20 pages.

Trivedi, "Mapping Relational Databases and SQL to MongoDB," https://code.tutsplus.com/articles/mapping-relational-databases-and-sql-to-mongodb--net-35650, Feb. 6, 2014, 15 pages.

* cited by examiner

200

Select Option:

201
- ☐ Life-sustaining Treatment
- ☐ Quality of life, at the expense of longevity
- ☐ Feeding tubes
- ☐ I do not want my family involved
- ☐ Other: _____

202
Whom would you want to speak for you if you were unable to speak for yourself:

_____

203
List Name and Email of two witnesses:

WITNESS ATTESTATION

I, ALEX JONES, hereby attest that I personally know JOHN SMITH, and that JOHN SMITH confirmed or signed this document in my presence, appearing to be of sound mind and under no duress.

☐ I agree

_____
Signature

FIG. 2B

LEGAL ADVANCE DIRECTIVE

I, JOHN SMITH, hereby appoint SARAH SMITH, to make medical decisions on my behalf in the event I cannot speak for myself.

I do not wish for Life-sustaining Treatment
I do not want feeding tubes

Signed:

JOHN SMITH

Witness 1
ALLEN JONES

Witness 2
MARY BART

301 { Property Address: _____

302 {
List Name and phone number of two witnesses:

PLANNING FOR YOUR CARE

If you were to become suddenly very sick or get into an accident, and were unable to speak for yourself, it is important for your healthcare team to understand your care preferences.

[Healthcare organization] is providing this tool free of charge which will:

- Help you to reflect on your values and what really matters to you in life, and create a written summary

- Name a healthcare agent who could speak for you if you were unable to do so, and create a legally-valid healthcare power of attorney form

- Share both documents with your healthcare team, healthcare agent, and anyone else you think should know.

| I need some time; remind me in a few days. | Continue |

NAME A HEALTHCARE AGENT                                                           706

A healthcare agent is someone that is legally authorized to speak with you if you were to become very sick and unable to speak for yourself.

A healthcare agent is someone who:

- you trust to make important healthcare decisions for you
- knows you well, and understands what matters to you in life
- can communicate effectively with your family and friends, who may have strong opinions about the care you should receive Do not choose a healthcare agent who:

- Provides healthcare to you, including anyone who owns or operates a healthcare facility where you receive care, or a relative of someone that provides care to you.

On the next screen, we'll ask you to name two individuals who could fulfill this role. The first is your primary healthcare agent; you will also be able to name an alternate agent, in case the primary agent is not able to serve in this capacity in the future.

If you'd like, you can take some time to speak to these individuals in advance. Or, if it's easier, we'll send a text or email to these individuals as a way to start the conversation.

| I need some time; remind me in a few days. | I am ready to name my healthcare agents |
|---|---|

NAME A HEALTHCARE AGENT

First Healthcare Agent

Name

Email

Mobile Phone Number

Personal Message

I need some time; remind me in a few days.

Accept and continue

REVIEW YOUR HEALTHCARE POWER OF ATTORNEY

My name is: JOHN SMITH   DOB: 12/3/1939

My healthcare agent is: MARY SMITH

My alternate healthcare agent is: ROBERT JONES

I have spoken to my agent and they know my goals and whishes as well as any content from guidance I have written. My agent has full authority to make healthcare decisions on my behalf in accordance with my goals and wishes in the event I am unable to speak for myself. In the event I am unable to communicate my wishes then my agent shall have broad authority to interpret my wishes to others in the medical community including:
1. To request that the medical community not treat me, withdraw care, or decide to conduct certain procedures and tests, or not, including surgical procedures. To also decide on my behalf if I should be put on life supporting mechanisms such as ventilation or artificial feeding and hydration or be resuscitated if I am in cardiopulmonary arrest. They have full authority to make these decisions on my behalf even if their decision may result in my death;

| I need some time; remind me in a few days. | Accept and Continue |

SIGN AND WITNESS THIS DOCUMENT

My Name Is:

You can also sign directly below with your mouse
(desktop) or finger pad (tablet)

| I need some time; remind me in a few days. |  |

716

NAME TWO WITNESSES THAT WILL ELECTRONICALLY SIGN

CLICK HERE TO SEE WHO CAN BE YOUR WITNESS

Name

Email

Mobile Phone Number

Name

Email

Mobile Phone Number

Go Back

SHARE THE NEWS AND MAKE YOUR PREFERENCES KNOWN!

Once all signatures have been obtained, we will automatically share this news with anyone you think should know, including your Primary Care Provider Name Email or phone number Name Email or phone number Primary Care Provider Fax Number Go Back

FIG. 7I

WITNESS SIGNATURE ⸺ 720

JOHN SMITH has asked to to digitally witness this document. To begin, your identity will first be verified by a third party service.

Before doing so, confirm you are NOT:

- Appointed as this individual's healthcare agent or back-up agent
- Related to the individual by blood, marriage, domestic partnership, or adoption, nor a spouse of any such person.
- A health care provider, including the owner or operator of a health, long-term care, or other residential or community care facility serving the individual
- An employee of the individual's health care provider
- Financially responsible for the individual's health care
- An employee of the individual's life or health insurance provider
- A creditor of the individual or entitled to any part of the individual's estate under a will or codicil, trust, insurance policy, or by operation of intestate succession laws.
- Entitled to benefit financially in any other way after the individual dies.

| I decline or am not qualified to serve as a witness | I confirm the above. Verify my identity |

SIGN THIS DOCUMENT AS WITNESS

My Name Is:

I declare that I personally know the person who signed this document, or I have been provided adequate proof of the person's identity, and that the person signed or acknowledged this Power of Attorney for Health Care in front of me, appearing to be of sound mind and under no duress, fraud, or undue influence.

You can also sign directly below with your mouse (desktop) or finger pad (tablet)

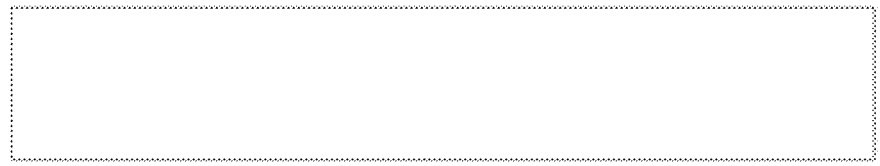

FIG. 7K

MULTIPLE ELECTRONIC SIGNATURE METHOD

CROSS-REFERENCE TO RELATED APPLICATIONS

This application claims the benefit of U.S. Provisional Application No. 62/674,136, filed on May 21, 2018, which is hereby incorporated by reference in its entirety herein.

This application is related to U.S. patent application Ser. No. 14/685,405, which was filed Apr. 13, 2015, which is entitled "System and Method for Documenting Patient Information", and which is hereby incorporated herein by reference in its entirety for any and all purposes.

This application is related to U.S. Pat. No. 9,881,201, which was filed on Jul. 14, 2015, which is entitled "Method and apparatus for collecting an electronic signature on a first device and incorporating the signature into a document on a second device", and which is hereby incorporated herein by reference in its entirety for any and all purposes.

This application is related to U.S. Pat. No. 9,679,190, which was filed on Jul. 7, 2016, which is entitled "Method and Apparatus for Collecting an Electronic Signature on a First Device and Incorporating the Signature into A Document on a Second Device", and which is hereby incorporated herein by reference in its entirety for any and all purposes.

This application is related to U.S. patent application Ser. No. 15/341,765, which was filed Nov. 2, 2016, which is entitled "Device Linking Method", and which is hereby incorporated herein by reference in its entirety for any and all purposes.

This application is related to U.S. patent application Ser. No. 15/204,960, which was filed Nov. 21, 2017, which is entitled "System and Method for Documenting Patient Information", and which is hereby incorporated herein by reference in its entirety for any and all purposes.

This application is related to U.S. patent application Ser. No. 16/304,399, which was filed on Nov. 29, 2018, which is entitled "Multiple Electronic Signature Method", and which is hereby incorporated herein by reference in its entirety for any and all purposes.

BACKGROUND

Many traditional documents requiring multiple signatures have been historically difficult to replicate in a digital context. In particular, ensuring all legal requirements to satisfy the process of witnessing signatures, for example for advance directive documents, has been a historical barrier to digitizing such documents.

SUMMARY

The disclosed device and method will enable the digital creation of documents requiring multiple signatures, particularly those in which dependencies exist between signatures and signatories, such as signatories who are witnesses to a primary signature. Additional configurations will be apparent to one of ordinary skill in the art in view of the teachings herein.

In an example, a method for securely collecting and managing advance care data. The method includes transmitting for rendering at a user device, a dashboard user interface having a plurality of sections relating to advance care planning for a user, wherein the dashboard user interface includes an advance directive user interface element for performing an operation relating to an advance care directive of the user; responsive to the advance directive user interface element being actuated, transmitting for rendering at a user device, an advance directive preferences user interface; receiving advance directive preferences data over the advance directive preferences user interface; after receiving the advance directive preferences data, transmitting for rendering at a user device, a first formalization user interface over which the user can provide signature data; receiving first signatory data from the user over the first formalization user interface; responsive to receiving the first signatory data over the first formalization user interface, initiating an additional signature data security process; and invalidating the first signatory data based on the additional signature data security process.

In an example, invalidating the first signatory data includes discarding the first signatory data. In an example, the method includes, after invalidating the first signatory data, notifying the user to provide signature data again over the first formalization user interface. In an example, the method further includes: after notifying the user, receiving further first signatory data from the user over the first formalization user interface; responsive to receiving the further first signatory data over the first formalization interface, reinitiating the additional signature data security process; and accepting the further first signatory data based on the reinitiated additional signature data security process. In an example, the method includes transmitting for rendering at the user device, a review user interface, wherein the review user interface includes a representation of an advance directive with the first signatory data and the additional signatory data applied. In an example, initiating the additional signature data security process includes starting a timer. In an example, the invalidating of the first signatory data is performed responsive to the timer expiring without receiving signature data from a witness. In an example, the method further includes receiving witness signatory data. The additional signature data security process can include a comparison of a witness signatory data location with a first signatory data location. In an example, the method further includes wherein the invalidating of the first signatory data is performed responsive to the witness signatory data location and the first signatory data location being more than a threshold distance apart. In an example, the method includes authenticating the user prior to transmitting the dashboard user interface. In an example, the operation includes creating, modifying, or revoking an advance directive.

In an example, there is a method for securely collecting and managing document data. In an example, the method includes: transmitting for rendering at a user device, a document preferences user interface; receiving document preferences data over the document preferences user interface; after receiving the document preferences data, transmitting for rendering at a first user device, a first formalization user interface over which a user can provide handwriting data; receiving first handwriting data from the user over the first formalization user interface; responsive to receiving the first handwriting data over the first formalization user interface, initiating an additional handwriting data security process; after initiating the additional handwriting data security process, receiving additional handwriting data from a second user device; based on the additional handwriting data security process, accepting the first handwriting data; after accepting the first handwriting data, generating a document based on the document preferences data; and applying the first handwriting data and the additional handwriting data to the document.

In an example, the method includes after applying the first handwriting data and the additional handwriting data to the document, locking the document to prevent further changes to the document. In an example, the method includes: after applying the first handwriting data and the additional handwriting data to the document, storing the document for later retrieval by the user. In an example, the document is a medical care document. In an example, the accepting of the first handwriting data is based on: (a) a timer, (b) locations associated with the first handwriting data and the additional handwriting data, or any combination of (a) and (b).

In an example, there is a non-transitory computer readable medium comprising instructions that, when executed by one or more processing units, cause the one or more processing units to perform a method for securely collecting and managing document data.

BRIEF DESCRIPTION OF THE DRAWINGS

It is believed the present invention will be better understood from the following description of certain examples taken in conjunction with the accompanying drawings, in which like reference numerals identify the same elements and in which:

FIG. 2A-2C illustrate exemplary user interfaces for completing a legal advance directive;

FIG. 3A-2C illustrate exemplary user interfaces for the completion of a real estate document;

FIGS. 7A-K illustrate an exemplary workflow and method for completing a goals-of-care document for healthcare with signature and witnesses in a fully electronic medium;

Figure 1:
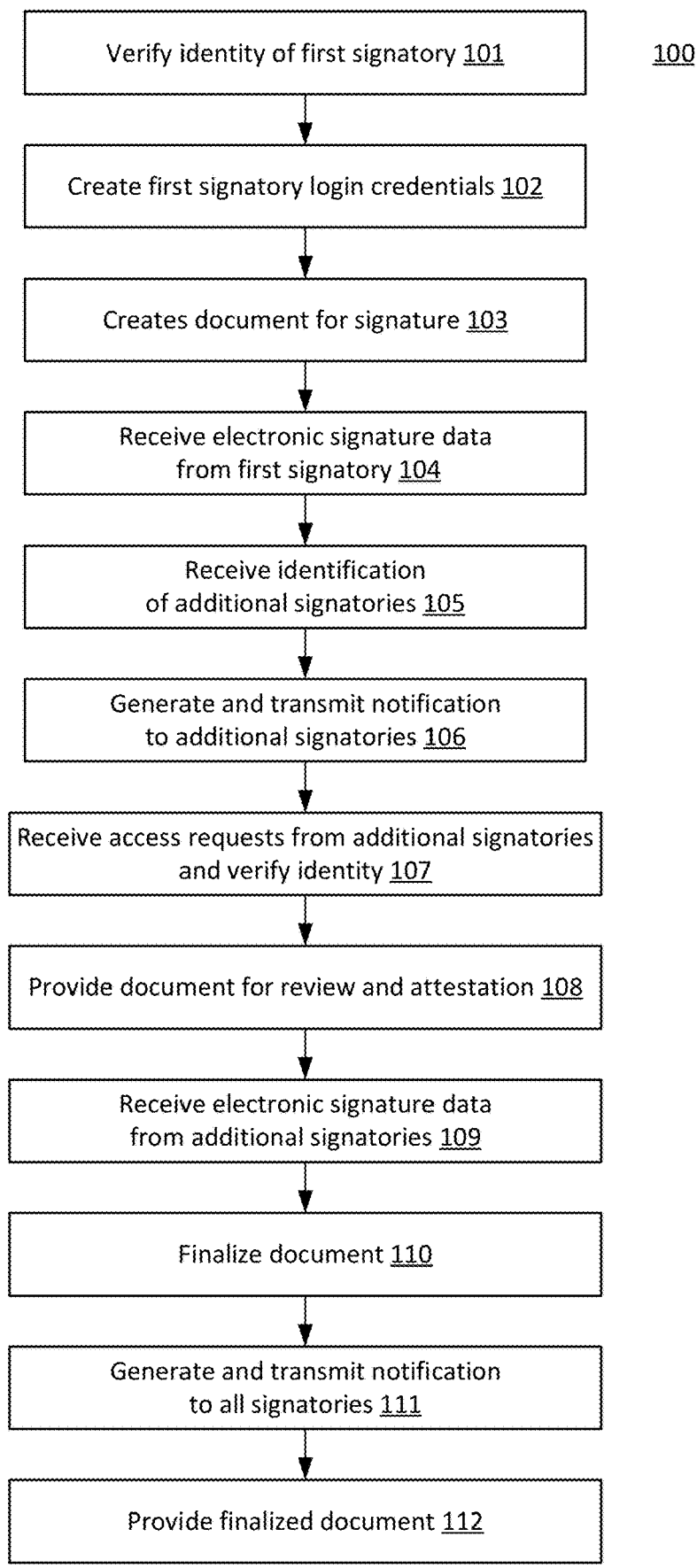
FIG. 1 illustrates an exemplary method of completing a document requiring witness signature.

Various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

An example method herein includes providing a document for review, verifying the identity of all signatories for the document, collecting a valid electronic signature, and collecting an attestation by one or more signatories. The process may, in certain embodiments, be facilitated through a networked (e.g., with access being provided via a website or application) documentation and signature system (which can be referred to as simply a "system"). In this way the signatories are not necessarily required to be in the same physical location, nor are they required to execute the signature at the same time. Rather, a signatory may simply be affirming that any functions, tasks, commitments, or other obligations contained in the attestation statement were completed prior to signature.

Various forms of documents may be reviewed, including, but not limited to contracts, advance directive, living wills, healthcare proxy forms, healthcare power of attorney documents, financial power of attorney, wills, and any other document where multiple signatories are required. Documents may be reviewed by some or all of the signatory, depending on the document type.

Identity verification may occur through a variety of techniques, including, but not limited to, knowledge-based methods (e.g., the signatory is challenged with one or more questions, the correct answers to which the signatory should be aware), biometric identification (e.g., verification by fingerprint, facial recognition, retinal recognition, voice recognition, heartbeat, genetic profile, or another form of biometric identification), verification using valid identifying documents (e.g., in-person or remote verification of the signatory against appropriate government-issued documents), or identification verification techniques known to those in the art. It should be noted that once identity verification has occurred, that a signatory may be authenticated through a uniquely assigned username and password or other unique identifying mechanism, such as a biometric identification. In certain embodiments, a signatory can generate knowledge-based identity verification questions for another signatory and such questions can be used to perform the identity verification process. These knowledge-based identity verification questions may ask the user questions about their personal history, credit history, or to solve for missing or purposefully-corrupted data such as correcting a digit in a phone number to one that is familiar to them.

The collection of a legally-valid electronic signature is well-described and known to those familiar with the art. Such electronic signatures generally comply with legal frameworks describing the requirements for a legally valid electronic signature.

The attestation of the signatory may include a variety of content depending on the context and purpose of the document to be signed. In the example of a signatory who is serving as a witness to a primary signatory, the attestation statement for the witness would include, for example, that he had confirmed or witnessed the actual signature of the document by the primary signatory. In the case of, for example, advance directives, the attestation may include additional parameters, including but not limited to statements affirming the primary signatory's soundness of mind, and lack of duress in signing the document. The attestation statement may or may not also include data from IP address, GPS location, or other confirmatory location based data that could improve the validity of the attestation statement where the user doing the attestation could include a time and location stamp with their attestation. In addition, the user doing the attestation can include an electronically-captured demonstration that the attesting party is in the same or similar physical location as the original signing party. The electronically-captured demonstration can be used to confirm that the signature witnessing at a physical location and time. The electronically-captured demonstration can take a variety of forms, including an image (e.g., a still image or an animated image, such as in the GIF format), video, or other electronically-captured medium. In some examples, the electronically-captured demonstration can be shared on or otherwise provided to a third-party social media platform (e.g., SNAPCHAT or INSTAGRAM) as evidence of the date or other parameters of the event. It should be noted however that in many instances an attestation statement on the part of the witnessing party that they confirm, swear, or hold an oath to the fact that they physically observed the signing party sign the document, may be all that is legally required to achieve the act of witnessing. We believe that the inclusion of an attestation of viewing or confirming the signing party's signature in a witness process of an electronic signature process is novel and not known to the art as is the inclusion of other confirmatory information as part of an attestation process as described herein.

FIG. 1 shows an exemplary method 100 by which a system can provide for receiving multiple electronic signature data. The method can begin with operation 101.

In operation 101, the system verifies the identity of a first signatory. For example, a first signatory accesses the system (e.g., via an Internet site) and undergoes an identity verification process 101. The identity verification can be performed in any of a variety of ways, including those described above. Generally, the identity verification can include the system receiving identity data from the first signatory and comparing the identity data against known identity data corresponding to the first signatory. If the received identity data is sufficiently similar to the known identity data, then the first signatory is verified. After the identity is verified, the user may optionally create credentials in the system, which is described in operation 102.

In operation 102, the system creates login credentials for the first signatory. For instance, the system can receive a username and password provided by the first signatory for future use in accessing the system. The system can process the username to ensure uniqueness in the system and can process the password to ensure sufficient strength. Following the creation of login credentials, the flow moves to operation 103.

In operation 103, the system facilitates the creation of an electronic document to be signed by the first signatory. In some examples, the system provides document editing features by which the first signatory can create the document. In some examples, the document editing features include templates that the first signatory can use as a starting point from which to create the document. Following the creation of the electronic document, the flow moves to operation 104.

In operation 104, the system receives electronic signature data from the first signatory signing the electronic document. The signing and the receipt of the signature can be accomplished in any of a variety of ways. In an example, the signature is received in the manner described in applicant's U.S. Pat. No. 9,679,190, filed Jul. 7, 2016, which is hereby incorporated by reference herein in its entirety for any and all purposes. Following operation 104, the flow moves to operation 105.

In operation 105, the system receives identification of additional signatories that will serve as witnesses. For example, the system may receive from the user the identities of two signatories. The identities can be specified in any of a variety of ways, including through the entry of a name, a phone number, an email address, an identification number, a physical address, other identifiers, or combinations thereof. Following operation 105, the flow can move to operation 106.

In operation 106, the system automatically generates a notification to each of the additional signatories and sends the notification to them. Each recipient's notification informs the recipient of the request for the recipient to serve as a witness. The notification can further include a link to an Internet site, mobile phone application, or another location associated with the system by which the recipient can act as a signatory. Following operation 106, the flow can move to operation 107.

In operation 107, the system receives access requests from each of the additional signatories (e.g., signatory #2 and #3). The system verifies the identities of the additional signatories and optionally creates credentials for them for later access (e.g., using one or more techniques described above in operation 101 and 102). Following operation 107, the flow can move to operation 108.

In operation 108, the system provides the additional signatories with all, part, or none of the document created in operation 104. The system can display the document for review by the additional signatories. The system further displays an attestation statement for review by the additional signatories. Once the attestation is reviewed by the additional signatories, the system receives electronic signature data from the additional signatories corresponding to the attestation. Following operation 108, the flow can move to operation 109.

In operation 109, the system provides a manner by which the additional signatories are able to sign the document. The system then receives electronic signature data from each of the additional signatories corresponding to the witness portion of the document. Following operation 109, the flow moves to operation 110.

In operation 110, the system finalizes the document after all signatories have signed the document. For example, the system can lock the document to prevent further changes to the document. Following operation 110, flow moves to operation 111.

In operation 111, the system can send a notification to all signatories. The notification can, for example, inform the recipient that the document is completed. The notification can further include a copy of the completed document or a link usable to access the completed document. The notification can be provided in any of a variety of ways, such as via email or instant message (e.g., SMS text message or via another messaging protocol). Following operation 111, the flow can move to operation 112.

In operation 112, the system provides access to the completed document to the signatories. For instance, the system can receive an access request from a signatory via a link sent in operation 111. The system can then determine whether the person accessing the link is authorized to view the document. For example, the system can confirm the identity of the person accessing the link using any of the techniques described herein. In this manner, the system can then provide each signatory or other authorized user access to the document for downloading, printing or transmission by any number of techniques. In other examples, the document can be saved by the system for later viewing.

FIGS. 2A, 2B, 2C show exemplary user interfaces for the creation of a legal advance directive. For example these user interfaces can be presented to the user in operation 103 described above and used to facilitate the creation of the document. FIG. 2A shows a user interface 200. The user interface 200 provides an area 201 that receives care preference choices in structured or unstructured free text format. The user interface 200 can also provide an area 202 for a user to specify a surrogate decision-maker. The user interface 200 can also provide an area 203 for a user to identify the name and contact information for witnesses for the document. FIG. 2B illustrates an exemplary user interface 210 for a witness, in which attestation statement data 214 is displayed. The user interface 210 can also include a user-actuatable click box 215 via which the user can actively attest to the attestation statement data 214. The user interface 210 further provides a region 216 for receiving the user's electronic signature. FIG. 2C illustrates a user interface 220 showing an example completed document. The completed document includes templated text 227 with a portion 228 populated based on the selections made in the user interface 200 of FIG. 2A. In addition, the document has a region 229 showing the signatures of the signatories.

Figure 3B:
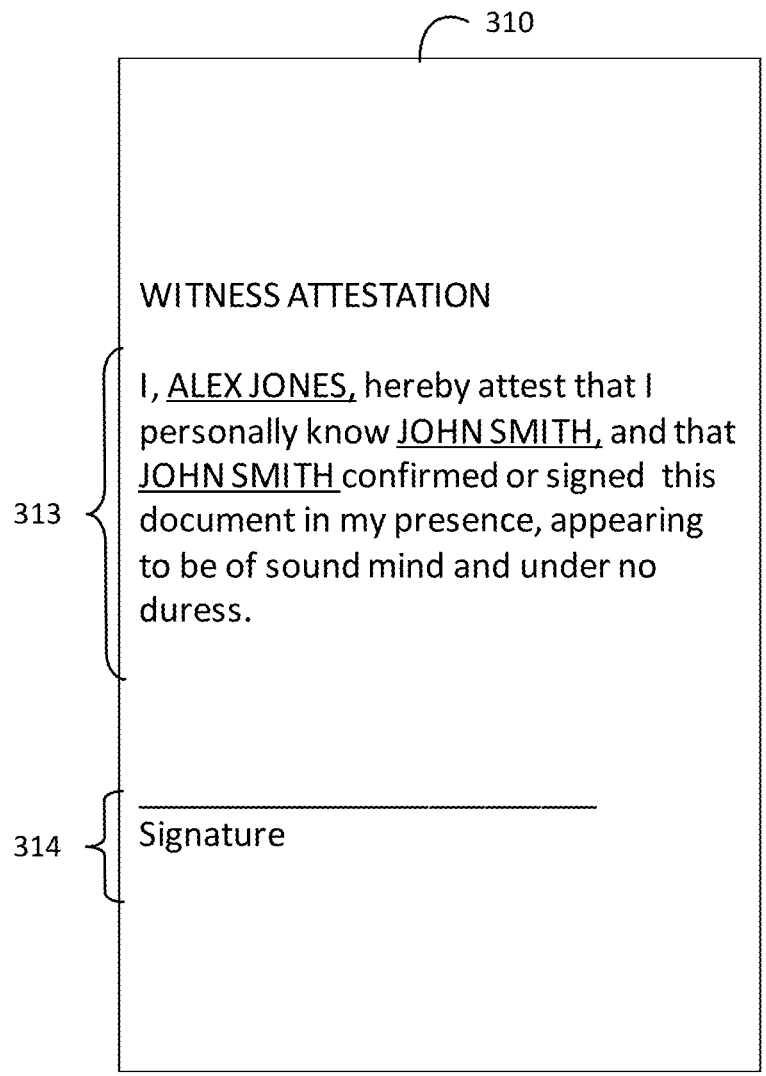
Figure 3C:
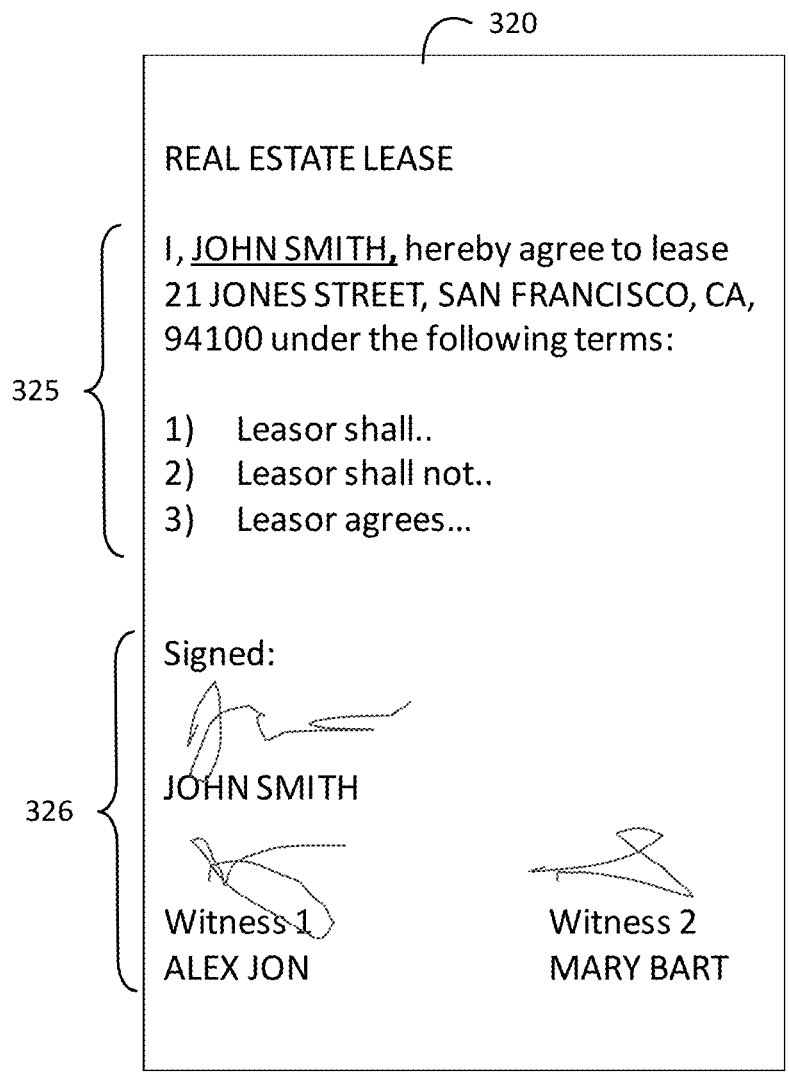

FIGS. 3A, 3B, 3C show exemplary user interfaces for the creation of a real estate transaction. FIG. 3A illustrates a user interface 300 having a portion 301 for receiving relevant information for a real estate transaction. The user interface 300 further includes a portion 302 for receiving identification (e.g., via a name and contact information) for witnesses for the document. FIG. 3B demonstrates and exemplary user interface 310 for a witness attestation. The user interface includes an attestation statement portion 313 and an electronic signature portion 314 where the witness can electronically provide a signature. FIG. 3C illustrates a user interface 320 showing a completed document. The document includes a template text portion 315 in which data from user interface 300 is populated. In addition, the signatories and their associated signatures are embedded and displayed in a signatory portion 326.

Figure 4:
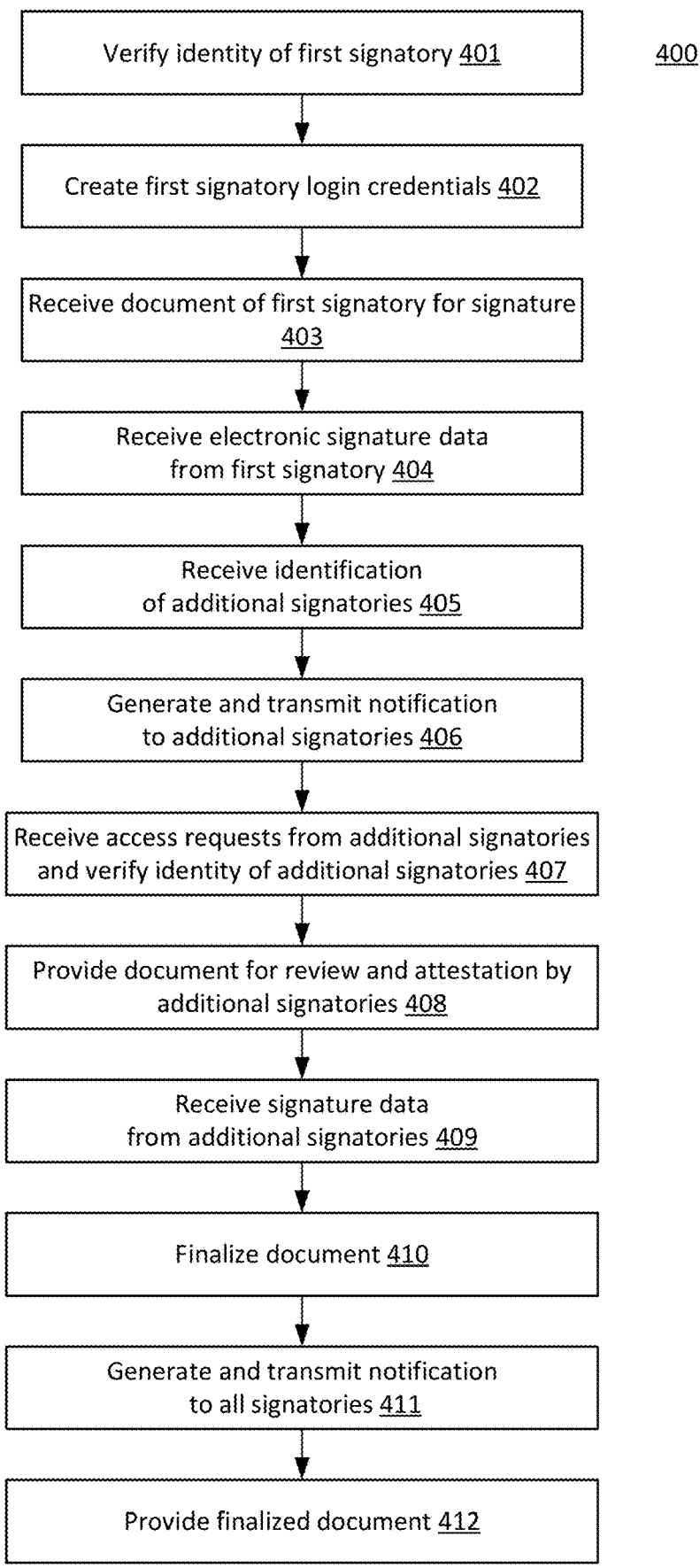
FIG. 4 illustrates an exemplary method of signing an uploaded document.

FIG. 4 shows an exemplary method 400 in which a first signatory accesses the system via a network, such as the Internet (e.g., via website). At operation 401, the system verifies the first signatory's identity (e.g., using a process previously described herein). Next, at operation 402, after the system verifies the first signatory's identity, the system allows the user to optionally create credentials with the system, such as with a username and password to access the system. At operation 403, the system receives a document provided by the first signatory. For example, the system can provide a way for the first signatory to upload a document, such as by providing a location for the first signatory to upload document. The document can be provided in the form of an image of a document, such as an image created using photo capture or scanning techniques in digital format and reviews it. At operation 404, the system obtains electronic signature data from the user to apply to the document. At operation 405, he first signatory identifies additional signatories (e.g., two additional signatories, such as signatory #2 and signatory #3) that will serve as witnesses. At operation 406, the system automatically generates and transmits a notification to each prospective signatory, notifying them of the request to serve as a witness. The notification can be transmitted using any of a variety of different mediums, such as via an instant message or an email. The notification can include a link that the additional signatories can use to access the system. At operation 407, the system receives individual access requests from the additional signatories. In response, the system can prompt the additional signatories for certain identifying information (e.g., a phone number or email addresses). The identifying information can be used to verify the identity of the person requesting access as being one of the additional signatories. The system can also create accounts to facilitate later access to the system for the additional signatories. At operation 408, the system provides the additional signatories with the document for review. The system can further provide the additional signatories with an attestation to be completed. At the operation 408, each additional signatory can independently review all, part or none of the document and completes the attestation. The attestation can be completed through any of a variety of techniques, such as via a user clicking on an agreement button. After the attestation is complete, in operation 409, the system individually prompts the additional signatories to electronically sign the document. Once the attestation is completed, each signatory #2 and #3 electronically signs the document. At operation 410, the system finalizes the document. Once the document is finalized, in operation 411 the system automatically notifies the signatories (e.g., via an email or instant message) that the document is completed and finalized. At operation 412, the system provides the signatories or other authorized users with the ability to access the document for downloading, printing, transmission, or other purposes. The system can save the document for later viewing or use.

Figure 5:
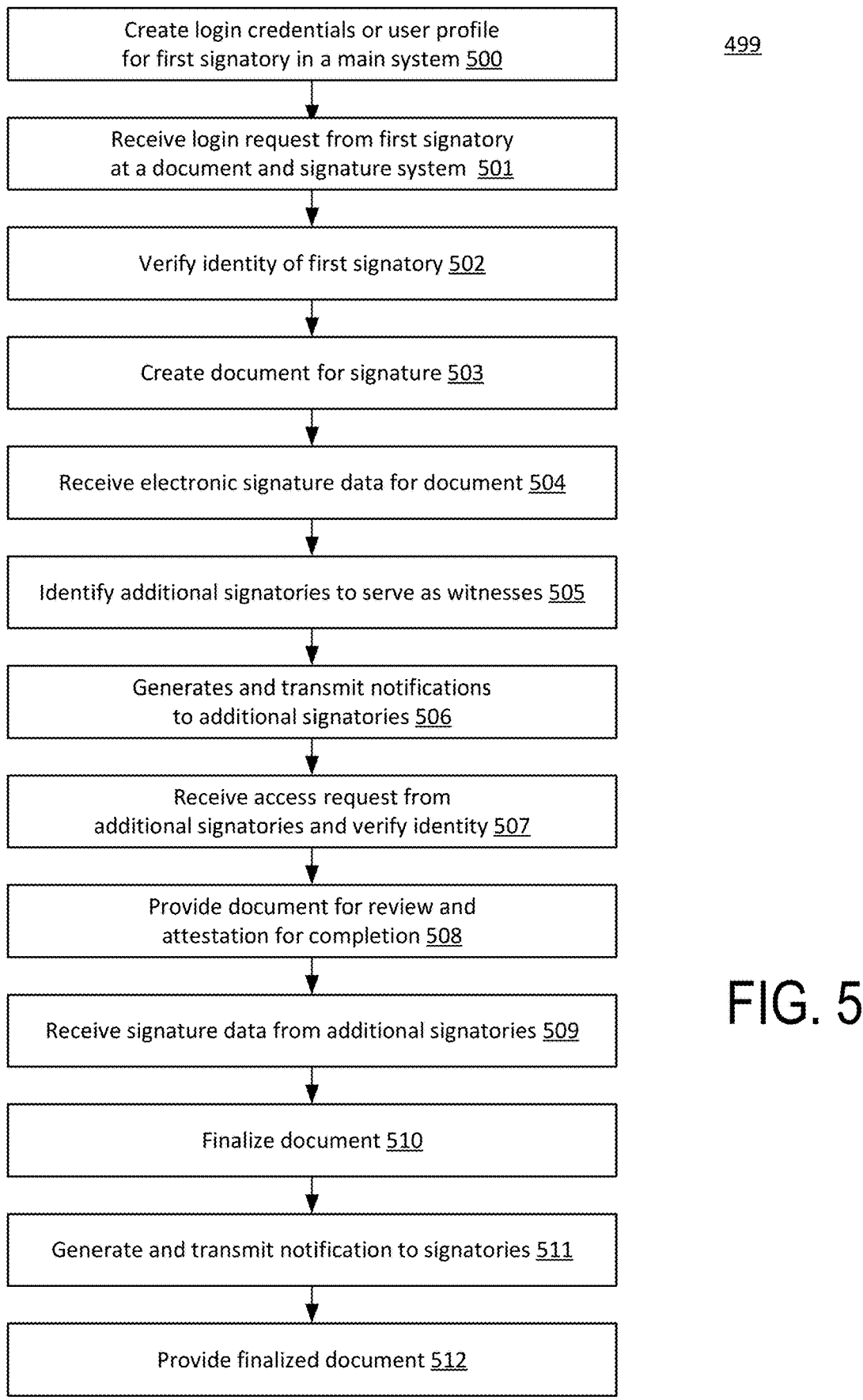
FIG. 5 illustrates an exemplary method of completing a document related to witness signature from a system with a single sign on approach from another system.

FIG. 5 shows an exemplary method 499. The method 499 includes operation 500 in which a main system receives login credentials or user profile data for a signatory from a system administrator of the main system. The main system then processes the received login credentials or user profile data such that the received credentials or data can be used in a single-sign-on process to log a user or the signatory into the signatory's profile into a documentation and signature system. Subsequently, in operation 501, the documentation and signature system receives a login request from a first signatory via a device (e.g., the phone, tablet, or computer of the first signatory or another person or entity). The login request can be provided via a single-sign-on link. For example, the first signatory can click on a single-sign-on link on the device to generate and provide the login request. At operation 502, the documentation and signature system verifies the identity of the first signatory. For instance, the documentation and signature system can prompt the first signatory to validate their identity independently or as part of a process of another user guiding the first signatory through a signing process. At operation 503, the system facilitates the creation of a document for the first signatory, such as by providing a text editor or a document-creation wizard. The first signatory then works to create and/or review the document individually or with others. In operation 504, the documentation and signature system provides a user interface for receiving signature data from the first signatory. The first signatory signs the document, thereby providing the signature data. In operation 505, the documentation and signature system provides a user interface for receiving identification data for additional signatories (e.g., second and third signatories). Using this user interface, the first signatory identifies additional signatories (e.g., two additional signatories) that will serve as witnesses and enters certain identifying information for the additional signatories (e.g., a phone number or email address). In operation 506, the documentation and signature system automatically generates a notification to each prospective signatory, notifying them of the request to serve as a witness. Next, in operation 507, the documentation and signature system receives access requests from the additional signatories. The documentation and signature system verifies the identity of the additional signatories and optionally creates credentials for the signatories to facilitate their later access of the documentation and signature system. In operation 508, the documentation and signature system provides each signatory with the ability to independently review all, part, or none of the document. For example, the documentation and signature system can present at least part of the document at a user interface for display to the additional signatories. The system further provides the additional signatory viewing the document with the ability to agree to an attestation statement, such as by clicking or tapping on a box or button of a user interface. In operation 510, once the attestation is completed, the documentation and signature system can provide the additional signatory that completed the attestation with the ability to electronically sign the document 509. The documentation and signature system receives signature data from the additional signatory. In operation 510, the documentation and signature system finalizes the completed document. In operation 511, the documentation and signature system automatically transmits notifications to all signatories (e.g., via a text or instant message) of the completion of the document. The documentation and signature system stores the completed document for later viewing or use. In operation 512, the documentation and signature system provides the completed document (e.g., at the request of the signatories). For instance, the documentation and signature system can allow each signatory or other authorized user to access the document for downloading, printing, transmission, or other use.

Figure 6:
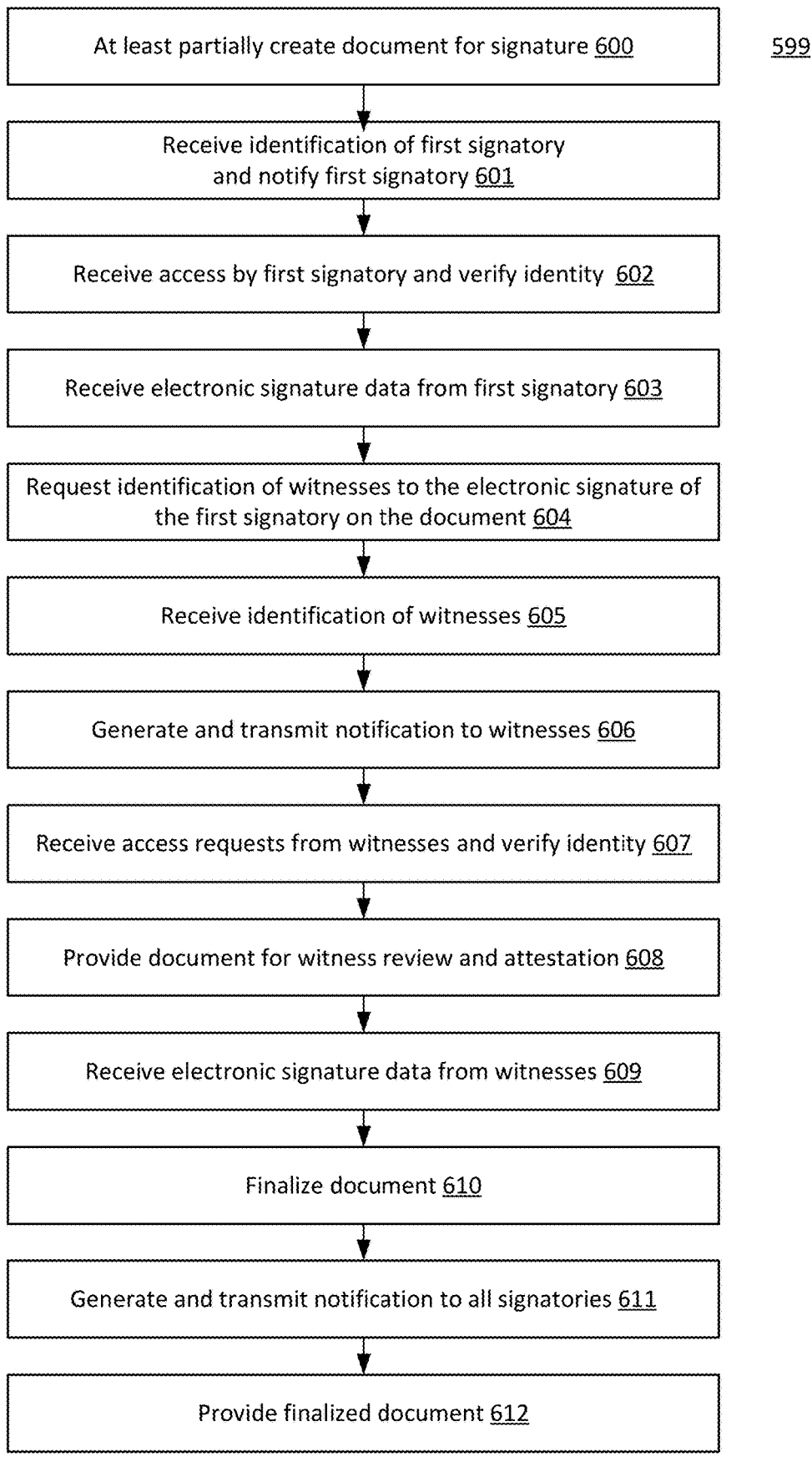
FIG. 6 illustrates an exemplary method of completing a document related to witness signature with a document preparer helping to guide the document creation process.

FIG. 6 shows an exemplary method 599. The method 599 can begin with operation 600 in which, the system logs in a document preparer. The system provides a user interface over which the document preparer can at least partially create a document or a template for signature to be signed. At operation 601, the system receives, from the document preparer, an identification of a first signatory. The system can receive the identification at any of a variety of times, such as before, during, or after the document or template is prepared. The system then notifies the first signatory that the document is available for their signature (e.g., notifying the first signatory that the document preparer is requesting their signature). At operation 602, the system receives a request from the first signatory and verifies that the request is from the first signatory (e.g., by verifying the identity of the requestor as being that of the first signatory). After the identity is verified, the system may receive credentials from first signatory (e.g., a username and password), which can facilitate later access to the system by the first signatory. At operation 603, the system provides the document to the first signatory (e.g., over a user interface) for review by the first signatory. The system further provides a user interface for receiving the signature of the first signatory. The first signatory can use the user interface to review the document and provide electronic signature data. At operation 604, the system notifies the first signatory or the document preparer that signature data of first signatory has been received and added to the document. The notification can further include a request to the first signatory or the document preparer to identify two witnesses to confirm the signature of the first signatory on the document. At operation 605, the system receives the identification of the additional signatories that will serve as witnesses. For example, the system can receive identifying information of the additional signatories. The identifying information can include, for example, a phone number or email address of the additional signatories. At operation 606, the system automatically generates a notification for each prospective additional signatory and transmits the notification. The notification informs the prospective additional signatories of the request to serve as a witness. At operation 607, the system provides the additional signatories with the ability to independently accesses the system and undergo identity verification. The system can also enable the additional signatories to create credentials to facilitate later access to the system. At operation 608, the system facilitates the display of the document to the additional signatories, so each additional signatory can independently reviews all, part, or none of the document. The system further provides the signatory with the ability to make or agree to an attestation statement. Once the attestation is completed, at operation 609, the system independently obtains signature data from each additional signatory. At operation 610, the system finalizes the document. At operation 611, the system generates and transmits a notification to (e.g., via email or instant message) to each of the signatories regarding the completion of the document. At operation 612, the system stores the document and provides each signatory or other authorized user with the ability to access the document for downloading, printing, transmission, or other use.

FIGS. 7A, B, C, D, E, F, G, H, I, J, K & L depict a series of screenshots of user interfaces for workflows from an exemplary process to complete a declaration of healthcare wishes in the form of a what-matters-most note. These healthcare wishes can include an advance healthcare directive, living will, power of attorney, or other medical legal order.

FIG. 7A illustrates an example user interface 702 having an overview and informational description that informs the patient that they are able to complete information now or wait until a later time. The user interface allows the user to make selection from these options via buttons. The system can record the user's selection to trigger follow up reminders or additional notifications to other accessing members of the system.

Figure 7B:
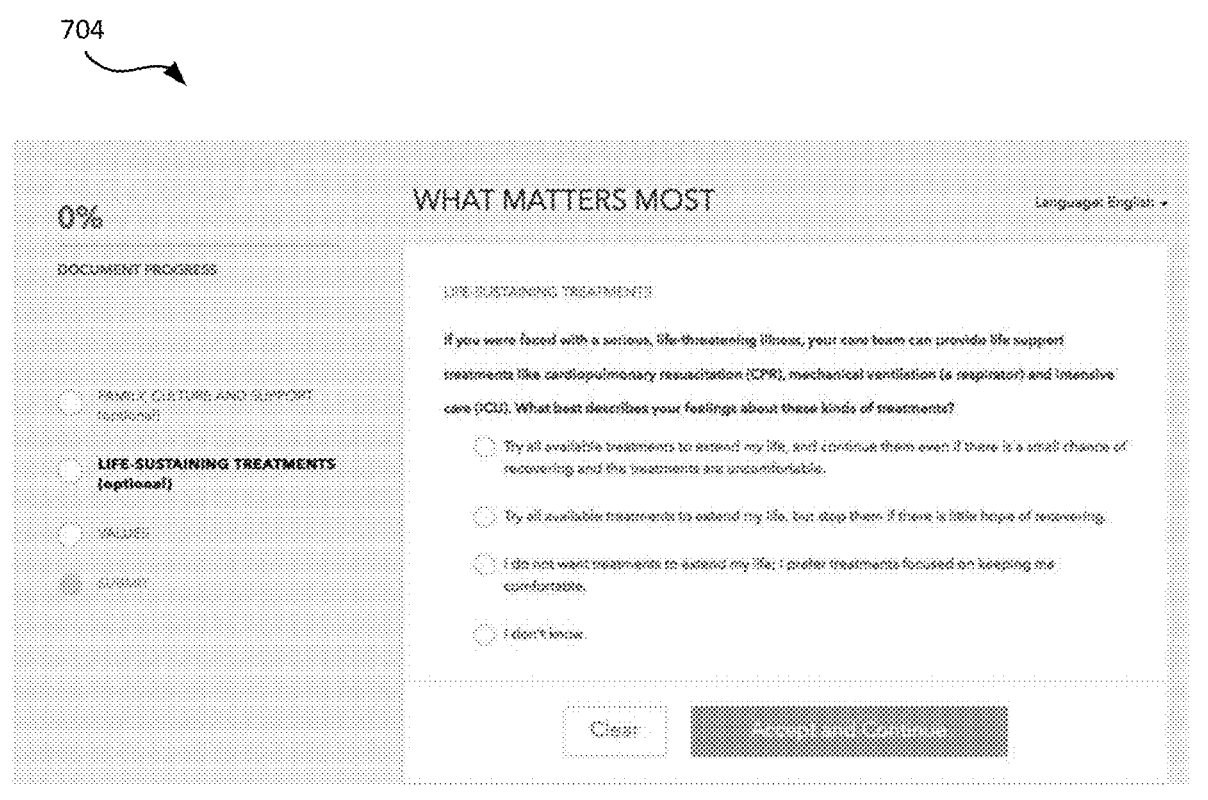

FIG. 7B illustrates is an illustrative example user interface 704 allowing a user to provide information regarding one of many types of medical legal documents that can be completed in conjunction with techniques described herein. As illustrated, the user interface enables the user to demonstrate the user's healthcare directives or medical orders by answering a series of questions or writing in responses. The user interface provides user interface elements for describing the user's responses to various questions. The system can record these answers and use them to generate a document or automatically populate fields within a template.

FIG. 7C illustrates a user interface 706 for a descriptive status indicator showing that the user needs to name a healthcare agent in order for their wishes to be valid. The user interface informs the patients about their legal rights and who they should name as their decision maker based on best practices. The user interface includes two buttons that the user can select to provide input.

FIG. 7D illustrates an example user interface 708 for a descriptive screen that allows the user to electronically provide the data regarding a healthcare agent. The user interface includes fields by which the user can provide a healthcare agent's name, email address, and phone number. The user interface further includes a field by which the user can enter a personal message to be sent to the healthcare agent. The data entered in this user interface can be used by the system to automatically generate a message to the healthcare agent to complete the signatory process electronically.

Figure 7E:
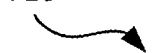

FIG. 7E illustrates an example user interface 710 by which the user can provide information regarding a second alternative healthcare agent. The data entered in this user interface can be used by the system to automatically generate a message to the healthcare agent to complete the signatory process electronically.

FIG. 7F illustrates an example user interface 712 for providing an attestation to be completed by the user. The illustrated attestation is that the healthcare agent (e.g., as specified in FIG. 7D or 7E) is known to the user and that the healthcare agent is informed of the user's medical wishes for care. The user interface provides a button by which the user can agree to allow that agent to act according to certain described guidelines that are medical and or legal in nature.

Figure 7G:
Figure 7G:

FIG. 7G illustrates an example user interface 714 for enabling a person to (e.g., a patient and or the patient's healthcare agent) to sign and witness the document. For example, the person can sign the document using a mouse, touchscreen, stylus, or another electronic signature method. In the illustrated example, the user interface provides a button the activation of which provides a mobile device linking method to allow a secondary device (e.g., a tablet or smartphone to be used to enter the signature remotely now or later). This process is described in applications and patents previously incorporated by reference, such as U.S. Pat. Nos. 9,679,190 and 9,881,201 and U.S. patent application Ser. No. 15/341,765.

FIG. 7H illustrates a user interface 716 that enables a signer to name two witnesses that will electronically sign and attest that they observed the signature process and know it to be true. The user interface provides fields for specifying the witnesses' names and contact information (as illustrated, their email address and phone number). The contact information can be used to send links or notifications to the witnesses (e.g., via a text message or email) regarding completion of the witnessing process. In some examples, the notifications or links can be sent securely or insecurely. Security can be enhanced by requiring authentication by a person following the link or instructions in a notification. For example, the system can require the user to scan a code (e.g., a QR code displayed on a screen of the device displaying the user interface of FIG. 7H) or by passing a challenge based question set that helps to authenticate the witness identity.

In an example, regarding the use of a code, the system can provide a code to a device used by the first signatory and require the witness to provide the same code via a device used by the witness. Responsive to the code provided by the witness being the same as the code provided for display at the device of the first signatory, an additional signature data security process can be satisfied. The witness can then be permitted to provide signature data. Responsive to the code not being the same, then an additional signature data security process can invalidate the first signatory data.

In an example, regarding passing a challenge, the system can provide one or more questions to a device used by the witness. Responsive to an answer provided by the witness matching an expected answer, an additional signature data security process can be satisfied. The witness can then be permitted to provide signature data. Responsive to a lack of matching, the additional signature data security process can invalidate the first signatory data.

FIG. 7I illustrates a sharing user interface 718. For example, a user can use the sharing user interface to share the user's wishes with broader individuals within the patient's network. As illustrated, the user interface include fields for receiving names and phone numbers of individuals to contact. The user interface further includes fields to specify a primary care provider and an associated fax number. The sharing user interface includes user-selectable buttons, including a button that, when activated, shares information regarding the document via various mediums, such as via email, fax, telephone (e.g., via voice or SMS message), or through social media accounts such as SNAPCHAT, TWITTER, FACEBOOK, or another social media network. In an example, this sharing user interface is displayed to a user once the final witness process has been completed. In another example, the sharing step can be performed by the patient prior to the witness signatures being accepted and the share notifications can be sent out automatically by the system after the final witness signatures are collected.

FIG. 7J illustrates a user interface 720 displaying an informational notification and legal guidelines for the witness to acknowledge and confirm prior to witnessing.

FIG. 7K illustrates a user interface 722 for a witness signature process where the document can be reviewed, the witness enters their name and then electronically signs with a noted attestation that they personally know who signed the document and or they have been given an indication of a person's identity and that they as the witness believe that person appears of sound mind and in no undue influence, duress, or fraud. In addition, that the witness attests that the person signing is physically in front of them at the time of signing if this is a legal requirement of witnessing in the location that the witnessing is taking place. The electronic signature could take place through any electronic signature mechanisms known in the art including through primary or secondary devices and the witness may be asked to answer identity based verification questions before or after this process of capturing a signature. This witness process can happen one or multiple times if multiple witnesses are required.

Figure 8:
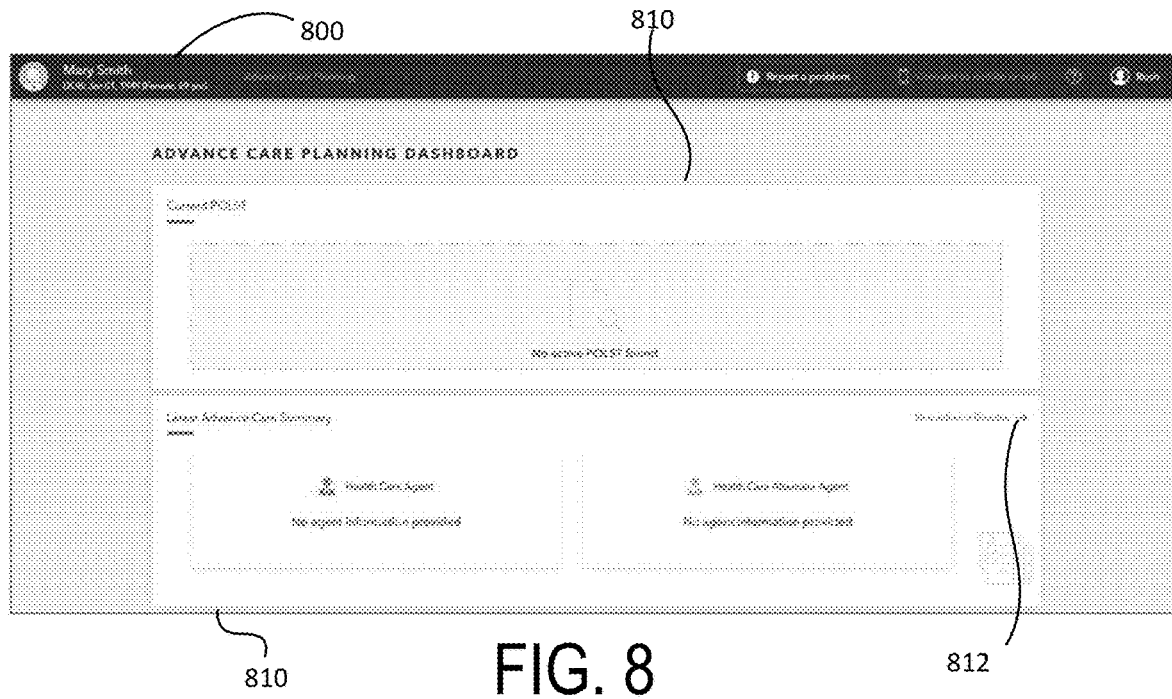
FIG. 8 illustrates an example advance care planning dashboard user interface.

FIG. 8 illustrates an example advance care planning dashboard user interface 800. The dashboard user interface 800 includes sections having advance care planning information for a current user. For example, the dashboard user interface 800 can include sections relating to life-sustaining treatment forms (e.g., a POLST form), advance directive forms, healthcare proxy forms, or other forms. The dashboard user interface 800 can further include additional information, such as contact information or a summary on a main portion 802 of the dashboard user interface 800. For example, the main portion of the dashboard user interface 800 is a portion of the dashboard user interface 800 that is first visible to the user when the dashboard user interface 800 is first rendered (e.g., after a user logs into or uses single sign on to access a system associated with the advance care planning dashboard from an electronic medical record, ePCR, or other system). As illustrated, a section 810 of the dashboard user interface 800 relating to an advance care directive includes an advance directive user interface element 812 (e.g., a user-actuatable button or arrow) for initiating a process for creating, modifying, or revoking an advance directive of the user.

Figure 9:
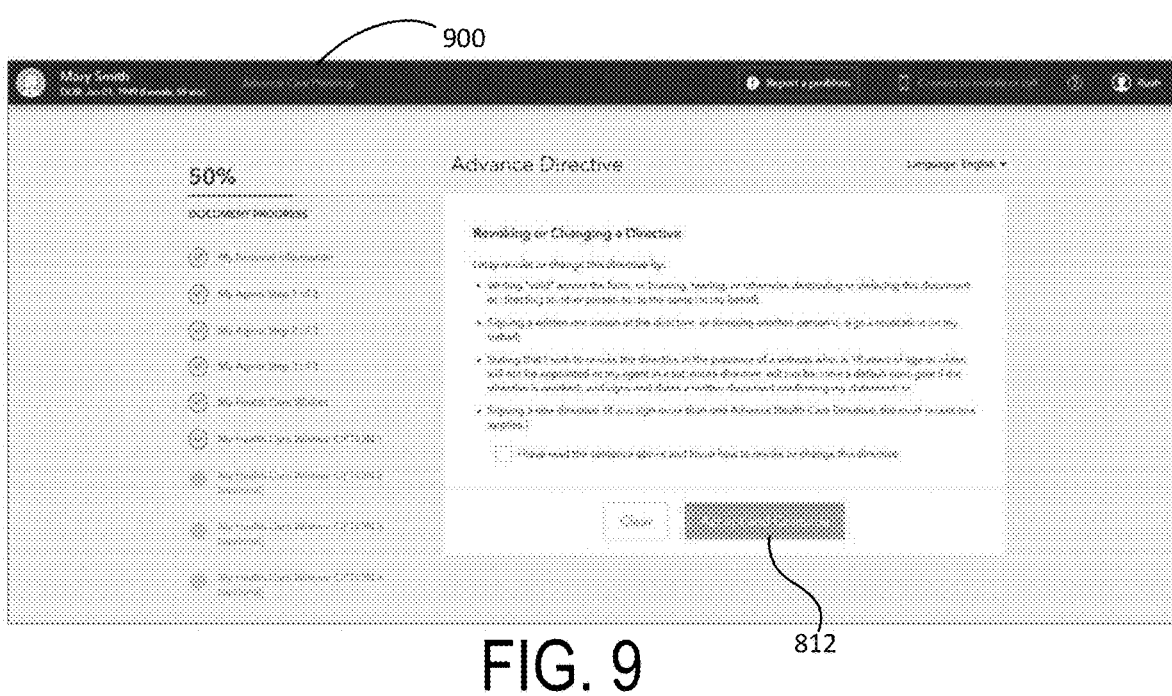
FIG. 9 illustrates a user interface related to a process for creating, modifying, or revoking an advance directive of a user.

FIG. 9 illustrates a user interface 900 related to a process for creating, modifying, or revoking an advance directive of a user. For example, the user interface 900 may be displayed responsive to the user actuating the user interface element 812. In certain examples, the process can require witnessing and or other forms of documentation beyond merely the signature of the subject of the advance directive. As illustrated, the user interface further includes a confirmation step that is achieved through actuation of a confirmation user interface element 902 such that a user needs to agree with the subject matter displayed on the user interface 900 in order to advance to the completion step or as part of a notification (e.g., without not necessarily being a requirement of advancing to a completion step).

Figure 10:
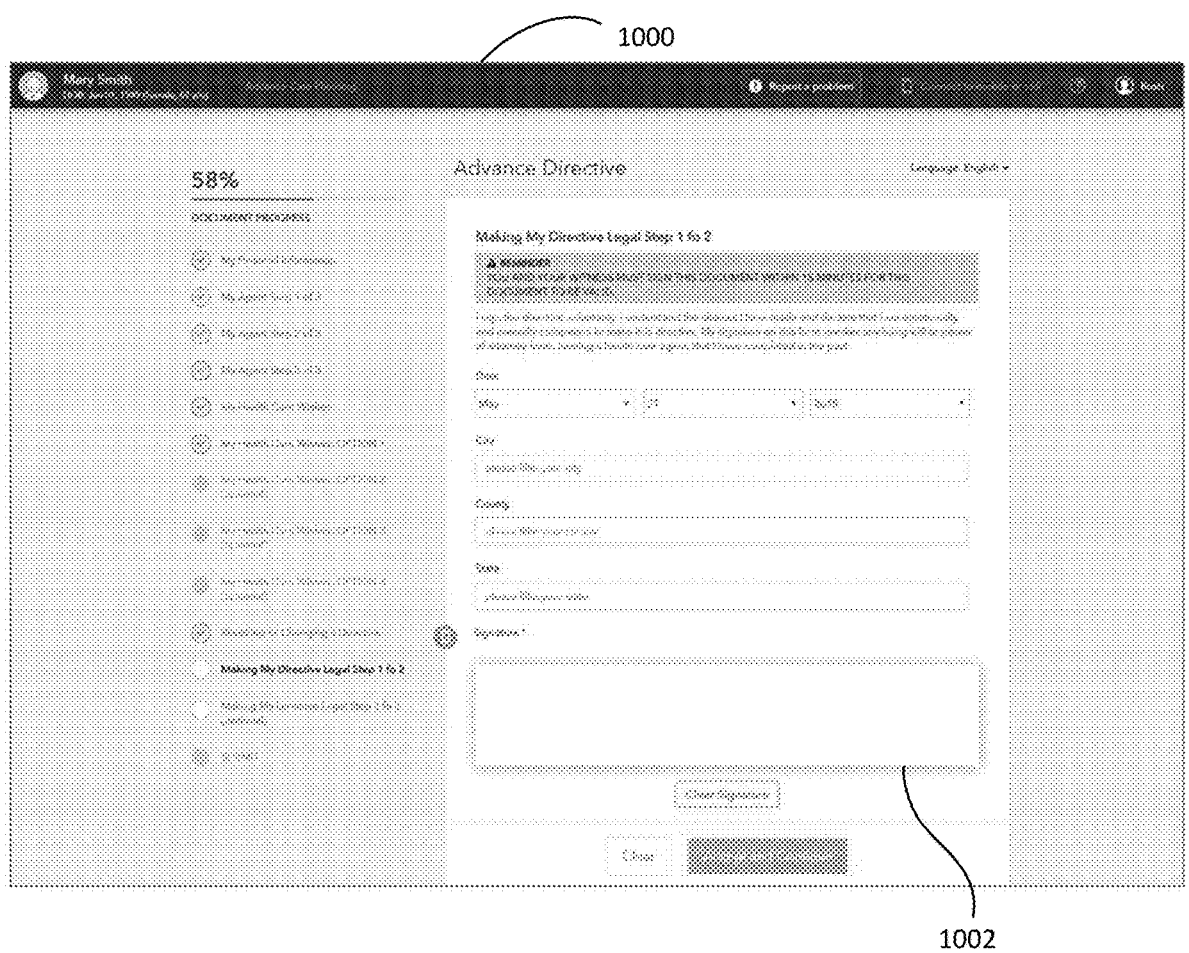
FIG. 10 illustrates a first formalization user interface.

FIG. 10 illustrates a first formalization user interface 1000. The first formalization user interface 1000 includes a set of user interface elements 1002 via which a first signatory (e.g., the person whose advance directive was being completed) can provide electronic signature data and one or more of date information and location information. In some examples, the date information is automatically populated in the date information portion of the user interface elements 1002 based on a current timestamp at a location of the user. Similarly, the location information can be filled in automatically based on location information automatically obtained by the user.

In an example, an action performed on the first formalization user interface 1000 (e.g., the actuation of an "accept and continue" button that advances to a next step in the advance directive planning process or the providing of the signature) initiates an additional signature data security process that enhances data integrity of the data provided. In an example, the data security process begins when the signatory provides electronic signature data. The initiation of the data security process can begin a limited time period in which an additional signatory is able to provide additional signatory electronic signature data. Responsive to the time period expiring without the receipt of the additional signatory electronic signature data, the system can automatically invalidates some or all of the advance directive. In an example, upon expiration, the system requires that the first signatory only repeat some or all of the formalization via the first formalization interface 1000 (e.g., simply providing electronic signature data again). This automatic invalidation can enhance the data security of the collected data by reducing the likelihood of false or inaccurate data being received and stored in association with the advance directive. Further, the additional signature data security process advantageously allows the system to maintain data integrity while providing additional flexibility in the manner in which signature data can be obtained. For example, the use of the additional signature data security process can be used to enable signature data to be provided from multiple different devices (e.g., thereby improving the user interface of the system and the ability of the system to collect data) while maintaining data integrity.

In addition to or instead of using a time period as part of the additional signature data security process, other data, such as the location data, can be used to enhance security. For example, a location of the first signatory when the electronic signature data is provided is compared with a location of one or more additional signatories when additional signature data is provided. If the additional signature data is provided from a geographic location sufficiently geographically close to the first signatory, then the additional signature data security process permits or accepts the additional signature data. If the additional signature data is provided from a geographic location sufficiently far (e.g., more than a predetermined threshold distance away), then the additional signature data security process can prevent an additional signatory from providing signature data. In addition or instead of preventing the additional signatory from providing signature data, the additional signature data security process can invalidate some or all of the data provided by the first signatory. In an example, the additional signature data security process can requires that the first signatory to only repeat some or all of the formalization via the first formalization interface 1000 (e.g., simply providing electronic signature data again). The location data can be provided using any of a variety of different techniques, such as via GPS or IP address information obtained from the respective devices. In another example, nearby SSIDs of wireless access points can be used to determine location or proximity. For instance, the first signatory and the additional signatories can be determined to be sufficiently close responsive to the devices from which the signature data is obtained are connected to a same wireless access point (e.g., as determined via an SSID or IP address) or have a sufficient number of nearby SSIDs in common (e.g., a threshold number of broadcast SSIDs from wireless access points are in common).

Figure 11:
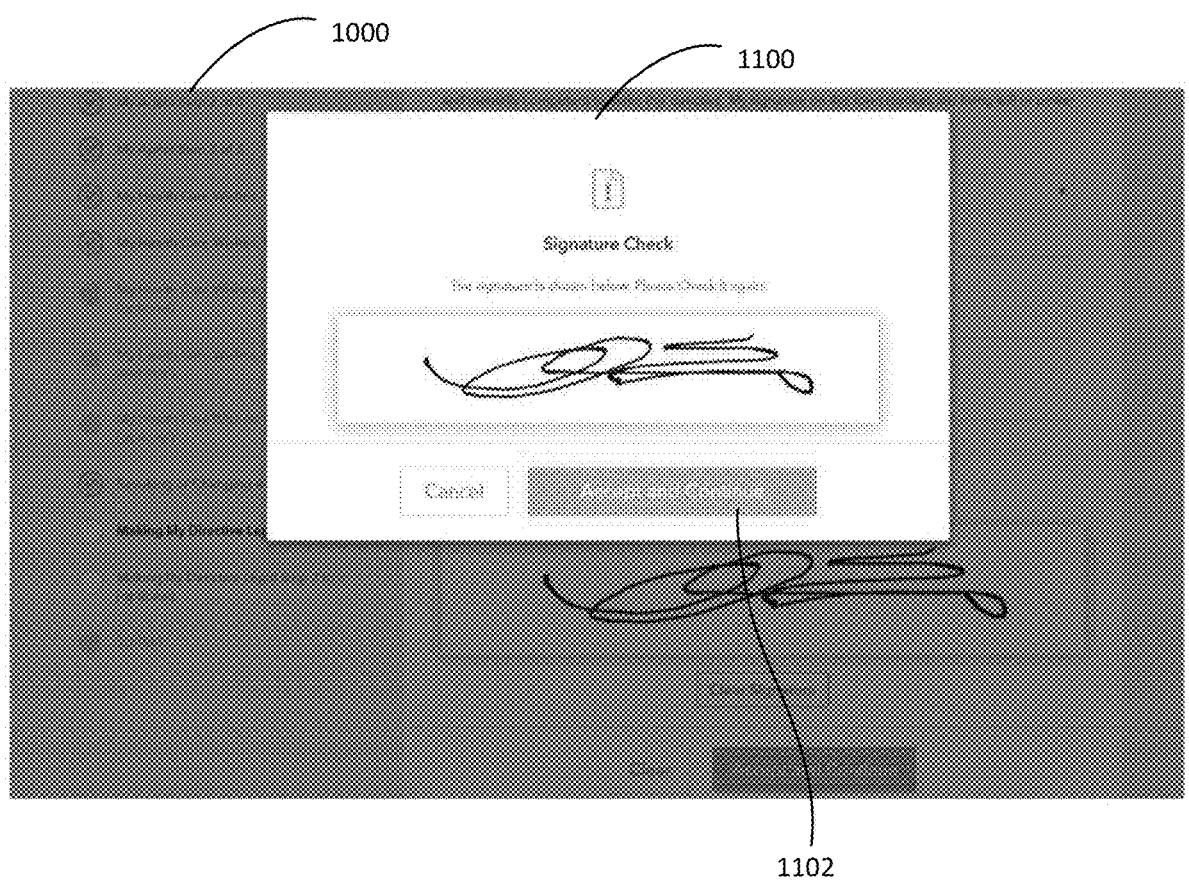
FIG. 11 illustrates a first signature confirmation user interface in which the signature data provided by the first signatory is displayed for review and acceptance by the first signatory.

FIG. 11 illustrates a first signature confirmation user interface 1100 in which the signature data provided by the first signatory is displayed for review and acceptance by the first signatory. For example, the first signatory can be required to review the signature data that the first signatory provided and then activate a confirmatory user interface 1102 element to confirm that they placed that signature on the screen. Activation of the confirmatory user interface element 1102 can start a timer associated with the additional signature data security process to allow for only a short allotted time for a witness to provide signature data for a witness's portion of the document for the witness's signature data to be valid or the first signatory would need to re-sign the document in their section and request the same or a new witness sign in the short allotted time. In the illustrated example, the first signature confirmation user interface 1100 is displayed as an overlay over the first formalization user interface 1000. In other examples, the confirmatory user interface element 1102 is added to the first formalization user interface 1000 responsive to the system receiving signature data from the first signatory without displaying the first signature confirmation user interface 1100.

Figure 12:
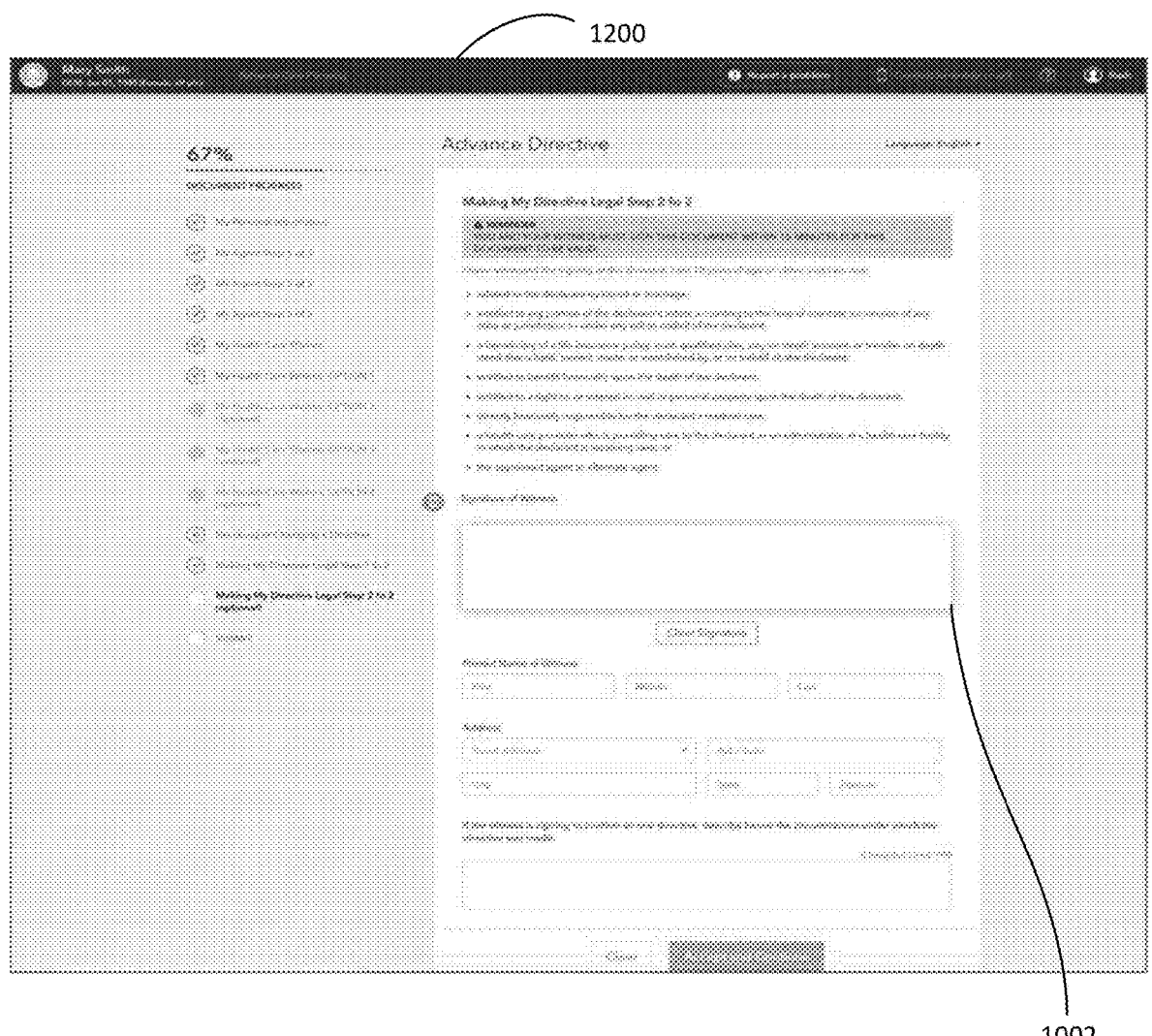
FIG. 12 illustrates a second formalization user interface 1200.

FIG. 12 illustrates a second formalization user interface 1200. The second formalization user interface 1200 can be displayed as part of a process for process for creating, modifying, or revoking a document, such as an advance directive. For example, document can be a document for which a witness to the first signatory's signature on the document is required (e.g., a healthcare power of attorney)

for the document to be legally enforceable. The second formalization user interface includes a user interface element 1202 via which signature data can be received from the witnesses. The witness can provide signature data in any of a variety of ways, such as via a mouse, touchscreen, stylus, click-through and pin, or linked mobile device.

As previously described, location information (e.g., a GPS location and based on a location described in an IP address) associated with the device displaying the second formalization user interface 1200 can be compared against the location data associated with the device that displayed the first formalization user interface 1000. The location comparison can be compared to determine that a user and a witness were within the same general proximity when completing and witnessing the document. This comparison can be used to improve data integrity and security.

In addition, a timer that was initially set in association with the first formalization user interface 1000 or the signature confirmation user interface 1100 (e.g., at the time the first signatory provided signature data) can be running. Timer information (e.g., an amount of time left or the time at which the timer expires) can be running in the background (e.g., the timer is invisible to the witness) or visible to the witness, such as by displaying a user interface element on the screen showing an amount of time left until the timer expires. In addition, visible or audible warnings can be provided regarding how soon the timer will expired (e.g., and as a result block the step of witnessing and/or require the witness and/or the first signatory to sign again, such as because it can be inferred that the witness did not witness the document signature from the first signatory within the allotted amount of time). This timer window can be matched to the time out parameters or settings on the web session for inactivity or a shorter or longer time as requested or demanded by the parties operating the system. The user interface 1100 can further provide for an attestation and or rule set that the witness must agree they adhere to when witnessing.

Figure 13:
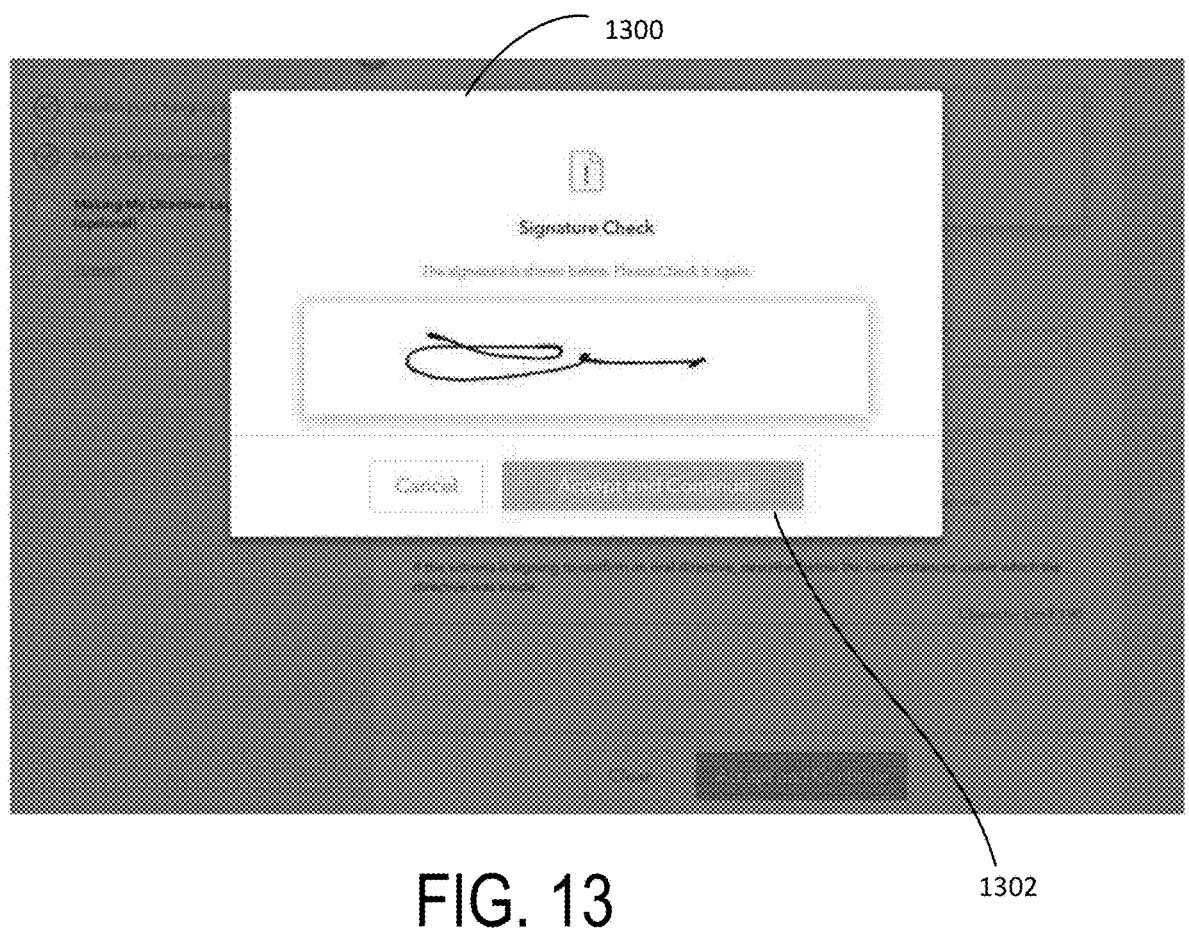
FIG. 13 illustrates a second signature confirmation user interface via which the witness can confirm that the signature data provided via the second formalization user interface, or other electronic signature method was confirmed.

FIG. 13 illustrates a second signature confirmation user interface 1300 via which the witness can confirm that the signature data provided via the second formalization user interface 1300, or other electronic signature method was confirmed. Once the signature is entered, the timer could be stopped and or the timer could still continue to run until the witness user confirms the signature data via this user interface 1300, such as by actuating a user interface element 1302. If the witness user does not confirm the signature in the allotted time the original signatory user could be forced to re-sign and the witness to re-witness and confirm within the allotted time to give some semblance that the witness was observing the signing individual at the time they signed the document and they appeared to be of sound mind and not under duress when signing on their behalf. Additional witnesses and or confirmation steps can be required if there are two witnesses or more. In an example, the system providing the user interface can perform integrity checks to ensure that the witnesses are not the same person. The integrity checks can improve the ability of the computer system to obtain useful and reliable data. The integrity checks can include, for example, ensuring that the handwriting signature and/or demographic or contact information of the witnesses are not identical. In this manner, it can be confirmed that there are unique witnesses that also attest to being legal witnessing powers.

Figure 14A:
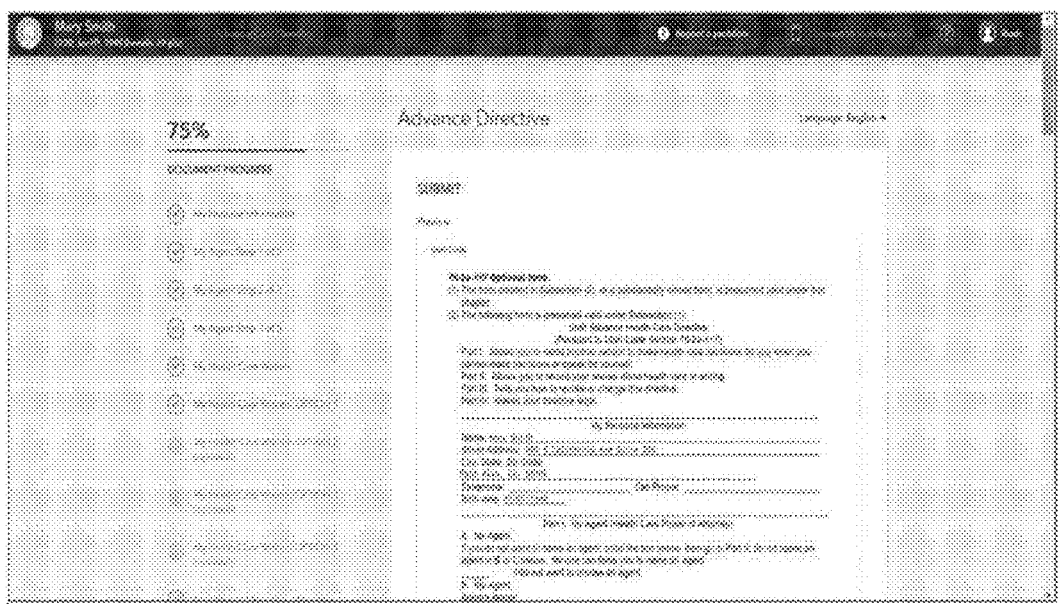
FIGS. 14A and 14B illustrate a review user interface.
Figure 14B:
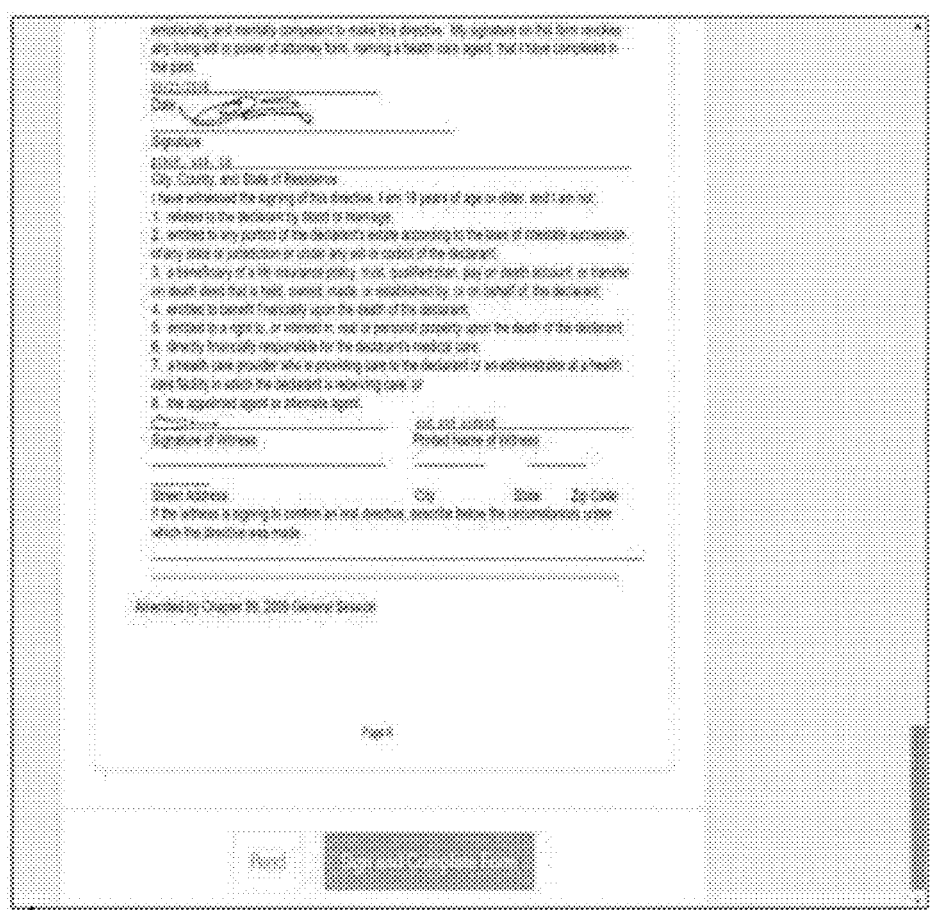

FIGS. 14A and 14B illustrate a review user interface 1400. The review user interface 1400 can be displayed to a user (e.g., the first signatory and/or the one or more witnesses) so the user can perform a final review step of the document after it has been signed and witnessed by the signatory and by the witness or witnesses. This review may also include reviewing that the actual signatures and or witness marks or signature marks were placed digitally on the page for later review of the final document. An additional timeout phase that may force re-signature can be used depending on the preferences of the authorizing user organization or the legal statutes in the geography in which the system is to be used.

Figure 15:
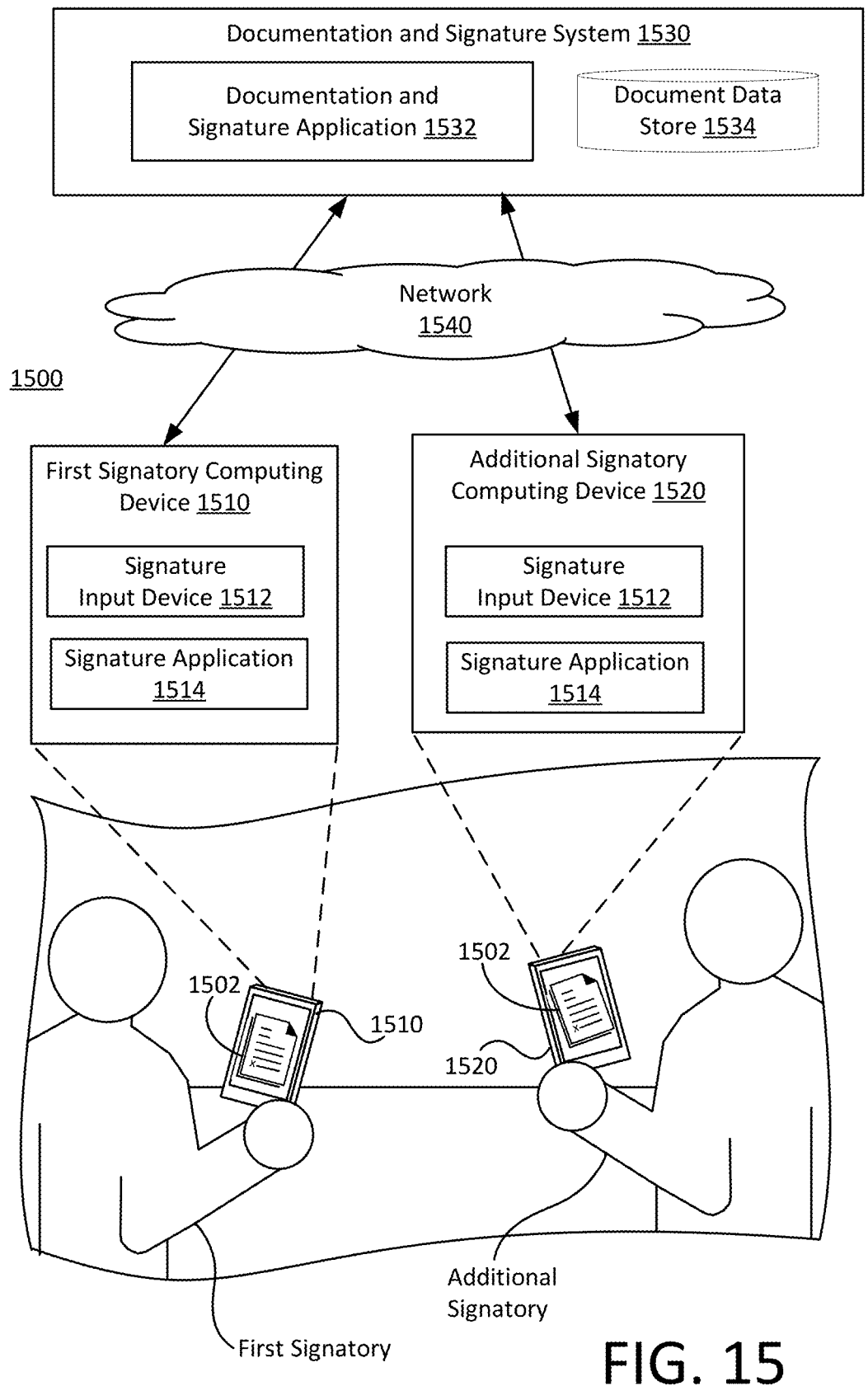
FIG. 15 illustrates an example environment in which aspects disclosed herein can operate.

FIG. 15 illustrates an example environment 1500 in which aspects disclosed herein can operate. As illustrated, the environment 1500 is one in which a first signatory and an additional signatory (e.g., a witness) are preparing to electronically sign (e.g., by providing electronic signature data) an electronic document 1502 via a first signatory computing device 1510 and an additional signatory computing device 1520, respectively. The environment 1500 further includes a documentation and signature system 1530 communicatively coupled to the computing devices 1510, 1520 via a network.

The computing devices 1510, 1520 can take any of a variety of forms (see, e.g., discussion of FIG. 17, below). In the illustrated example, the computing devices are smartphones having at least a signature input device 1512 and operating a signature application 1514.

The signature input device 1512 is a device or component of the computing device 1510 or 1520 over which signature data can be obtained. In many examples, the signature input data is obtained in the form of handwriting input data (e.g., data representing handwriting of the user, such as one or more paths defining movement of a stylus, pen, or finger controlled by the user) via a touch screen (e.g., a capacitive or resistive touch screen), a stylus-sensitive component (e.g., a screen or pad configured to receive input from a stylus), a mouse, or another component. The obtaining of the signature data from the signature input device 1512 can be facilitate via the signature application 1514.

The signature application 1514 is an application at least partially running on the computing device 1510, 1520 to facilitate the signing of the document 1502. The signature application 1514 can take any of a variety of forms. In many examples, the signature application 1514 is implemented using computer-executable instructions stored and running at least partially on the computing devices 1510, 1520. In many examples, the signature application 1514 cooperates with the documentation and signature system 1530. The signature application 1514 can be or include a native application operating on the computing device 1510, 1520. In other examples, the signature application 1514 is a browser-based application operating in a browser window of the computing devices 1510, 1520. The signature application 1514 can be configured to display one or more of the user interfaces described herein and receive input from a user. Further, the signature application can transmit data obtained over the user interfaces to the documentation and signature system 1530.

The documentation and signature system 1530 is a computing system that can be configured to perform one or operations described herein with respect to a system or documentation and signature system. The system 1530 can be implemented as a computing system of one or more virtual or physical server computers. In the illustrated example, the system includes a documentation and signature application 1532. The application 1532 can perform one or more operations described herein relating to documents and obtaining signatures. In examples, the application 1532 cooperates with the signature application 1514 to provide data to and receive input from a user. In the illustrated example, the documentation and signature system 1530 further includes a document data store 1534 (e.g., implemented at least in part as a database or via another data structure) configured to store documents. The document data store 1534 can store complete or incomplete documents. The document data store 1534 can further store templates for documents.

Figure 16:
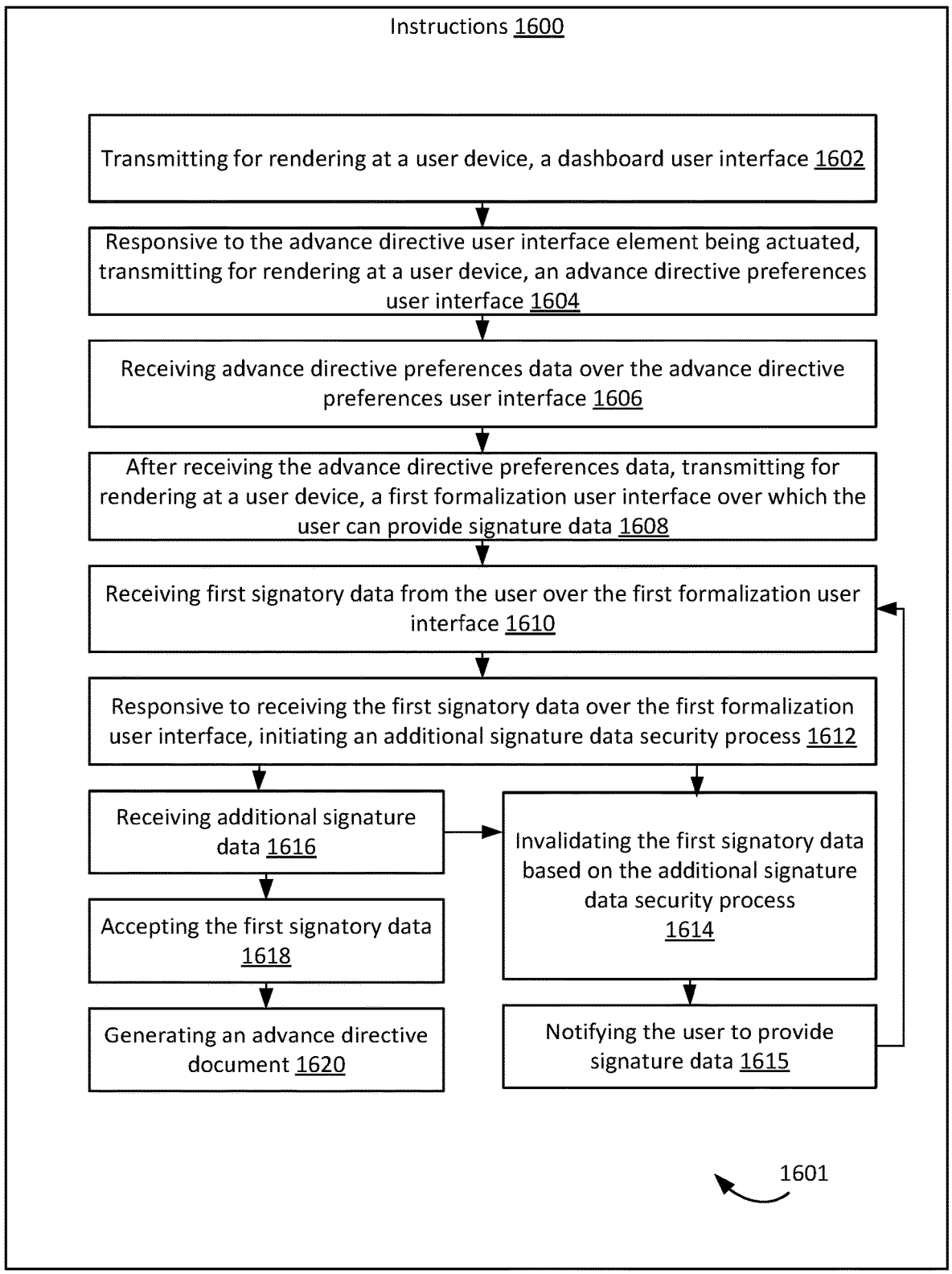
FIG. 16 illustrates instructions that, when executed, cause performance of a method for securely collecting and managing advance care data.

FIG. 16 illustrates instructions 1600 that, when executed, cause performance of a method 1601 for securely collecting and managing advance care data. The method 1601 can be performed using or in conjunction with one or more of the aspects disclosed above. In examples, the method is partially or entirely performed by a system, such as a documentation and signature system (e.g., documentation and signature system 1530). The method 1601 includes operations, including operation 1602. In an example, the documentation and signature system 1530 includes a server having memory with the instructions 1600 stored thereon. In an examples, the method 1601 is performed at least in part by the documentation and signature application 1532. While the method 1601 is described primarily in the context of advance care directives, at least similar techniques can be used in the context of documents in general. Similarly, while the method 1601 describes signature data, the method 1601 can be used with other data, such as handwriting data.

Operation 1602 includes transmitting for rendering at a user device, a dashboard user interface (e.g., advance care planning dashboard user interface 800). In some examples, the dashboard user interface is transmitted responsive to authenticating a user. User interface data can be transmitted in any of a variety of ways, such as by transmitting user interface data over a network (e.g., network 1540) to a user device (e.g., the first signatory computing device 1510) configured to render the user interface data. The dashboard user interface can include a plurality of sections relating to advance care planning for a user. In an example, the dashboard user interface includes an advance directive user interface element (e.g., advance directive user interface element 812) for performing an operation relating to an advance care directive of the user. In examples, the operation can include creating, modifying, or revoking an advance directive. Following operation 1602, the flow can move to operation 1604.

Operation 1604 includes responsive to the advance directive user interface element being actuated, transmitting for rendering at a user device, an advance directive preferences user interface (e.g., user interface 704). In an example, the device rendering the advance directive user interface element detects input (e.g., a click or a tap) from a user that actuates the user interface element. The user device can then transmit data indicating the actuation. The data indicating the actuation is received. In response, an advance directive preferences user interface can be transmitted. Following operation 1606, the flow can move to operation 1606.

Operation 1606 includes receiving advance directive preferences data over the advance directive preferences user interface. In an example, the advance directive preferences data can be specified via any of a variety of user interface elements, such as text fields, buttons, check boxes, or radio buttons, among others. Following operation 1606, the flow can move to operation 1608.

Operation 1608 includes after receiving the advance directive preferences data, transmitting for rendering at a user device, a first formalization user interface (e.g., user interface 1200) over which the user can provide signature data. Following operation 1608, the flow can move to operation 1610.

Operation 1610 includes receiving first signatory data from the user over the first formalization user interface. In an example, receiving the first signatory data includes receiving handwriting data corresponding to a signature of the user. Following operation 1610, the flow can move to operation 1612.

Operation 1612 responsive to receiving the first signatory data over the first formalization user interface, initiating an additional signature data security process. In an example the additional signature data security process is as described above. For instance, initiating the additional signature data security process can include starting a timer. In another example, the additional signature data security process relates to location. For instance, the additional signature data security process includes a comparison of an additional signatory data location with a first signatory data location. Following operation 1612, the flow can move to operation 1614 or operation 1616.

Operation 1614 includes invalidating the first signatory data based on the additional signature data security process. The invalidating can take any of a variety of forms. For example the invalidating the first signatory data can include discarding or deleting the first signatory data. In an example, invalidating the first signatory data is performed responsive to the timer expiring without receiving signature data from a witness (e.g., as may be referred to as "additional signature data"). In an example, the invalidating of the first signatory data is performed responsive to the witness signatory data location and the first signatory data location being more than a threshold distance apart. Following operation 1614, the flow can move to operation 1615.

Operation 1615 includes notifying the user to provide signature data. The notifying can be performed via any of a variety of ways, such as via a user interface element. Following operation 1615, the flow can return to operation 1610. For instance, after notifying the user, the further first signatory data can be received from the user over the first formalization user interface. Responsive to receiving the further first signatory data over the first formalization interface, the additional signature data security process can be reinitiated. Ultimately the further first signatory data can be accepted based on the reinitiated additional signature data security process.

Operation 1616 includes receiving additional signature data. In some examples, the additional signature data is received from a witness to the first signature data being provided. In some examples, the additional signature data is received from a device (e.g., an additional signatory computing device) different form the device from which the first signatory data is provided (e.g., the first signatory computing device 1510). Following operation 1616, the flow can move to operation 1618.

Operation 1618 includes accepting the first signatory data. In examples, accepting the first signatory data includes approving the first signatory data for use with the advance care directive. For example, the first signatory data can be flagged or otherwise indicated as being acceptable for use with the advance care directive. Following operation 1618, the flow can move to operation 1620.

Operation 1620 includes generating an advance directive document. In some examples, generating the advance directive document can include obtaining an advance directive document template and populating fields within the template with data based on the advance directive preferences data. In some examples, generating the advance directive document includes applying the signature data to the document. In some examples, the generating of the advance directive document can include transmitting for rendering at the user device, a review user interface. The review user interface can include a representation of the advance directive (e.g., with the first signatory data and the additional signatory data applied) for final confirmation of the user prior to the document being finalized.

Figure 17:
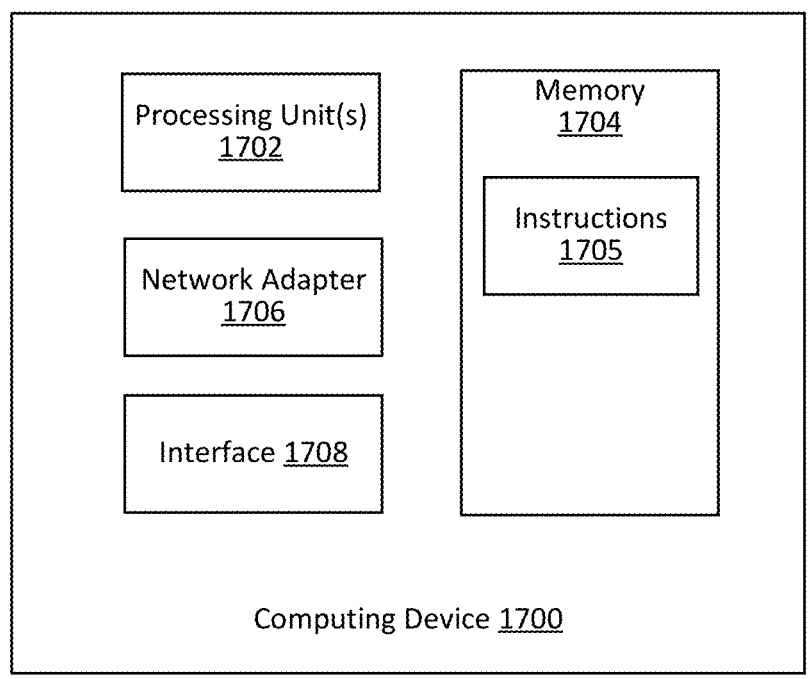
FIG. 17 illustrates an example of a suitable computing device with which one or more of the disclosed examples can be implemented.

FIG. 17 illustrates an example of a suitable computing device 1700 with which one or more of the disclosed examples can be implemented. Computing devices, systems, environments, or configurations that can be used with examples described herein include, for example, smartphones, tablets, desktop computers, laptop computers, server computers, hand-held devices, smart watches, multiprocessor systems, microprocessor-based systems, programmable consumer electronics, and distributed computing environments, among other examples. The computing device 1700 can be a virtual or physical device. The computing device can operate over a network or directly with one or more other computing devices, such as a server, a personal computer, a router, or a peer device, among other examples. In examples, the first signatory computing device 1510, the additional signatory computing device 1520, and the server 1530 include one or more components or variations of components of the computing device 1700.

In the illustrated configuration, the computing device 1700 includes one or more processing units 1702, memory 1704, a network adapter 1706, and an interface 1708. The computing device 1700 can include other components, such as a system bus, component interfaces, a graphics system, a power source (e.g., a battery), among other components. Other configurations are also possible.

The one or more processing units 1702 can include one or more hardware or virtual processors (e.g., central processing units) configured to obtain and execute instructions. The one or more processing units 1702 can communicate with and control the performance of other components of the computing system 1702. For example, the one or more processing units 1702 can cause the interface 1708 to provide output to a user.

The memory 1704 is one or more virtual or physical computer-readable storage media operable to store information accessible by the processing unit 1702. The memory 1704 can be transitory, non-transitory, or combinations thereof. The memory 1704 can be volatile (e.g., RAM), non-volatile (e.g., ROM), or combinations thereof. At least some of the memory 1704 can be removable or non-removable. Indeed, the memory 1704 can take any of a variety of different forms including but not limited to: random access memory, read-only memory, electronically-erasable programmable read only memory, flash memory, optical memory, disc-based memory, magnetic-based memory, solid-state memory, or any other memory media usable to store information for later access. In some examples, the memory 1704 can, at least in part, be remote from the one or more processing units 1702. For instance, the memory 1704 can include memory accessible via the network adapter 1706 and take the form of a wired or wireless media. The memory 1704 can store, among other things, instructions 1705 executable by the one or more processing units 1702 to cause execution of applications. The memory 1704 can store instructions 1705, that when executed by the one or more processing units 1702 cause performance of operations described herein, such as described above in relation to FIGS. 1, 4-6, and 16.

The network adapter 1706 is a component of the computing device 1700 that enables the computing device 1700 to access other computing devices, such as via a network. The network adapter 1706 can provide wired or wireless network access. The network adapter 1706 facilitate network access via one or more of a variety of communication technologies and protocols, such as ETHERNET, cellular, BLUETOOTH, near-field communication, and radiofrequency communication, among others. The network adapter 1706 can include one or more antennas and associated components configured for wireless communication according to one or more wireless communication technologies and protocols.

The interface 1708 is one or more devices configured to receive input or provide output. For example, the interface 1708 can include input devices over which the computing device 1700 receives input from a user, the environment, or another device. The input devices can include, for example, physically-actuatable user-interface elements (e.g., buttons, switches, or dials), touch screens, keyboards, mice, pens, and voice input devices, among others input devices. The interface 1708 can further include one or more output devices by which the computing device 1700 is able to provide output to a user, the environment, or another computer. The output devices can include, for example, one or more displays, speakers, and printers, among other output devices.

While particular uses of the technology disclosed herein have been discussed primarily in the context of advance directives and other medical care documents, the disclosed technology can be used with a variety of contexts. The above disclosure is not meant to suggest that the disclosed technology is only suitable for use with systems, user interfaces, and processes similar to those illustrated in the figures. In general, additional configurations can be used to practice the methods and systems herein. Further, some aspects (e.g., portions, components, operations, etc.) described can be excluded without departing from the methods and systems disclosed herein.

This disclosure describes some aspects of the technology with reference to the accompanying figures, in which only some of the possible aspects were shown. Other aspects can be embodied in many different forms and should not be construed as being limited to the aspects set forth herein. Rather, the aspects were provided so that this disclosure was thorough and complete and fully conveyed the scope of the possible aspects to those skilled in the art.

The various aspects described with respect to the figures herein are not intended to limit the systems and methods to the particular aspects described. Accordingly, additional configurations can be used to practice the methods and systems herein and/or some aspects described can be excluded without departing from the methods and systems disclosed herein.

Similarly, where steps or operations of a process or method are disclosed, they are described to illustrate the present methods and systems without limiting the disclosure to a particular sequence of operations. For example, the operations can be performed in differing orders, two or more operations can be performed concurrently, additional operations can be performed, and disclosed operations can be excluded without departing from the present disclosure.

Although specific aspects are described herein, the technology's scope is not limited to those specific aspects. One skilled in the art will recognize that other aspects or improvements are within the scope of the present technology as well. Thus, the specific structure, acts, or media are disclosed only as illustrative aspects. The scope of the technology is defined by the following claims and any equivalents therein.

What is claimed is:

1. A method for securely collecting and managing advance care data, the method comprising:
transmitting, for rendering at a user device, a dashboard user interface having a plurality of sections relating to advance care planning for a user, wherein the dashboard user interface includes an advance directive user interface element for performing an operation relating to an advance care directive of the user;
responsive to the advance directive user interface element being actuated, transmitting, for rendering at a user device, an advance directive preferences user interface;
receiving advance directive preferences data over the advance directive preferences user interface;
after receiving the advance directive preferences data, transmitting, for rendering at a user device, a first formalization user interface over which the user can provide signature data;
receiving first signatory data from the user over the first formalization user interface;
responsive to receiving the first signatory data over the first formalization user interface, initiating an additional signature data security process;
automatically determining a requirement for an attestation to be included with the additional signature data security process for the advance care directive, the requirement being based upon a location of the attestation, wherein the additional signature data security process includes a comparison of a witness signatory data location with a first signatory data location; and
invalidating the first signatory data based on the additional signature data security process, wherein the invalidating of the first signatory data is performed responsive to the witness signatory data location and the first signatory data location being more than a threshold distance apart.

2. The method of claim 1, wherein invalidating the first signatory data includes discarding the first signatory data.

3. The method of claim 1, further comprising, after invalidating the first signatory data, notifying the user to provide signature data again over the first formalization user interface.

4. The method of claim 3, further comprising:
after notifying the user, receiving further first signatory data from the user over the first formalization user interface;
responsive to receiving the further first signatory data over the first formalization user interface, reinitiating the additional signature data security process; and
accepting the further first signatory data based on the reinitiated additional signature data security process.

5. The method of claim 4, further comprising transmitting, for rendering at the user device, a review user interface, wherein the review user interface includes a representation of an advance directive with the first signatory data and the additional further first signatory data applied.

6. The method of claim 1, wherein initiating the additional signature data security process includes starting a timer, and wherein the invalidating of the first signatory data is performed responsive to the timer expiring without receiving signature data from a witness.

7. The method of claim 1, further comprising authenticating the user prior to transmitting the dashboard user interface.

8. The method of claim 1, wherein the operation includes creating, modifying, or revoking an advance directive.

9. A method for securely collecting and managing document data, the method comprising:
transmitting, for rendering at a user device, a user interface;
receiving user input data over the user interface;
after receiving the user input data, transmitting, for rendering at a first user device, a first formalization user interface over which a user can provide handwriting data;
receiving first handwriting data from the user over the first formalization user interface;
responsive to receiving the first handwriting data over the first formalization user interface, initiating an additional handwriting data security process;
automatically determining a requirement for an attestation to be included with the additional handwriting data security process, the requirement being based upon a location of the attestation, wherein the additional signature data security process includes a comparison of a witness signatory data location with a first signatory data location;
invalidating first signatory data based on the additional signature data security process, wherein the invalidating of the first signatory data is performed responsive to the witness signatory data location and the first signatory data location being more than a threshold distance apart;
after initiating the additional handwriting data security process, receiving additional handwriting data from a second user device;
based on the additional handwriting data security process, accepting the first handwriting data;
after accepting the first handwriting data, generating a document based on the user input data; and
applying the first handwriting data and the additional handwriting data to the document.

10. The method of claim 9, wherein the user interface comprises a document preferences user interface, and wherein the user input data comprises user document preferences data.

11. The method of claim 9, further comprising, after applying the first handwriting data and the additional handwriting data to the document, locking the document to prevent further changes to the document.

12. The method of claim 9, further comprising, after applying the first handwriting data and the additional handwriting data to the document, storing the document for later retrieval by the user.

13. The method of claim 9, wherein the document is a medical care document.

14. The method of claim 9, wherein the accepting of the first handwriting data is based on: (a) a timer, (b) locations associated with the first handwriting data and the additional handwriting data, or any combination of (a) and (b).

15. A non-transitory computer-readable medium comprising instructions that, when executed by one or more processing units, cause the one or more processing units to:
transmit, for rendering at a user device, a document preferences user interface;
receive document preferences data over the document preferences user interface;
after receiving the document preferences data, transmit, for rendering at a first user device, a first formalization user interface over which the user can provide handwriting data;

receive first handwriting data from the user over the first formalization user interface;

responsive to receiving the first handwriting data over the first formalization user interface, initiate an additional handwriting data security process;

automatically determine a requirement for an attestation to be included with the additional handwriting data security process, the requirement being based upon a location of the attestation, wherein the additional signature data security process includes a comparison of a witness signatory data location with a first signatory data location;

invalidating first signatory data based on the additional signature data security process, wherein the invalidating of the first signatory data is performed responsive to the witness signatory data location and the first signatory data location being more than a threshold distance apart;

after initiating the additional handwriting data security process, receive additional handwriting data from a second user device;

based on the additional handwriting data security process, accept the first handwriting data;

after accepting the first handwriting data, generate a document based on the document preferences data; and apply the first handwriting data and the additional handwriting data to the document.

16. The non-transitory computer-readable medium of claim 15, wherein the instructions, when executed, further cause the one or more processing units to, after applying the first handwriting data and the additional handwriting data to the document, lock the document to prevent further changes to the document.

17. The non-transitory computer-readable medium of claim 15, wherein the instructions, when executed, further cause the one or more processing units to, after applying the first handwriting data and the additional handwriting data to the document, storing the document for later retrieval by the user.

18. The non-transitory computer-readable medium of claim 15, wherein the document is a medical care document.

19. The non-transitory computer-readable medium of claim 15, wherein the accepting of the first handwriting data is based on: (a) a timer, (b) locations associated with the first handwriting data and the additional handwriting data, or any combination of (a) and (b).

* * * * *